United States Patent
Krappmann et al.

(10) Patent No.: US 9,504,692 B2
(45) Date of Patent: Nov. 29, 2016

(54) SELECTIVE INHIBITION OF MALT1 PROTEASE BY PHENOTHIAZINE DERIVATIVES

(75) Inventors: Daniel Krappmann, München (DE); Daniel Nagel, München (DE); Dolores Schendel, München (DE); Stefani Spranger, Chicago, IL (US)

(73) Assignee: HELMHOLTZ ZENTRUM MUNCHEN, DEUTSCHES FORSCHUNGSZENTRUM FUR GESUNDHEIT UND UMWELT (GMBH), Neuherberg (DE)

( * ) Notice: Subject to any disclaimer, the term of this patent is extended or adjusted under 35 U.S.C. 154(b) by 0 days.

(21) Appl. No.: 14/235,755

(22) PCT Filed: Aug. 1, 2012

(86) PCT No.: PCT/EP2012/065072
§ 371 (c)(1),
(2), (4) Date: May 15, 2014

(87) PCT Pub. No.: WO2013/017637
PCT Pub. Date: Feb. 7, 2013

(65) Prior Publication Data
US 2014/0288060 A1 Sep. 25, 2014

(30) Foreign Application Priority Data
Aug. 2, 2011 (EP) .................................... 11006346

(51) Int. Cl.
| | | |
|---|---|---|
| A61K 31/5415 | (2006.01) |
| C07D 279/12 | (2006.01) |
| A61P 19/02 | (2006.01) |
| A61P 17/06 | (2006.01) |
| A61P 25/28 | (2006.01) |
| A61P 35/00 | (2006.01) |
| A61K 31/546 | (2006.01) |

(52) U.S. Cl.
CPC ......... *A61K 31/5415* (2013.01); *A61K 31/546* (2013.01); *C07D 279/12* (2013.01)

(58) Field of Classification Search
CPC .................. C07D 513/04; A61K 31/5415
USPC ............... 544/35, 37, 38, 41, 42; 514/224.8, 514/225.2
See application file for complete search history.

(56) References Cited

U.S. PATENT DOCUMENTS

| | | | |
|---|---|---|---|
| 3,156,692 A | 11/1964 | Müslin et al. |
| 2005/0192274 A1 | 9/2005 | Borisy et al. |
| 2006/0009506 A1 | 1/2006 | Westwick et al. |

FOREIGN PATENT DOCUMENTS

| | | |
|---|---|---|
| EP | 0138481 A2 | 4/1985 |
| EP | 0889037 A1 | 1/1999 |
| GB | 774882 A | 5/1957 |
| JP | 60155165 | 8/1985 |
| JP | H110508826 A | 9/1998 |
| JP | 2004517915 A | 6/2004 |
| JP | 2007535510 A | 12/2007 |

(Continued)

OTHER PUBLICATIONS

Vippagunta et al., Advanced Drug Delivery Reviews 48: 3-26, 2001.*
Ulrich J. Kirk-Othmer Encyclopedia of Chemical Technology, pp. 1-7, 2002.*
McAllister-Lucas et al. Clin Cancer Res. Nov. 1, 2011; 17(21): 6623-6631.*
Ohlow et al. Drug Discovery Today vol. 16, Nos. 3/4, Feb. 2011.*
Freshney et al.,Culture of Animal Cells, A Manual of Basic Technique, Alan R. Liss, Inc., 1983, New York, p. 4.*
Dermer et al., Bio/Technology, 1994, 12:320.*
Cecil Textbook of Medicine, edited by Bennet, J.C., and Plum F., 20th edition,vol. 1, 1004-101 O, 1996.*
Hailfinger et al. "Essential role of MALT1 protease activity in activated B cell-like diffuse large B-cell lymphoma" Proceedings of the National Academy of Sciences, National Academy of Sciences US, vol. 106, No. 47, (Nov. 24, 2009). pp. 19946-19951.
International Search Report and the Written Opinion of the International Searching Authority, or the Declaration; PCT/EP2012/065072 ; by applicant company Helmholtz Zentrum München Deutsches Forschungszentrum fur Gesundheit und Umwelt (GmbH); Nov. 6, 2012.
Zhelev et al. "Phenothiazines suppress proliferation and induce apoptosis in cultured leukemic cells without any influence on the viability of normal leukocytes." Cancer Chemotherapy and Pharmacology, Springer Verlag, Berlin, vol. 53, No. 3, (Mar. 1, 2004); pp. 267-275.

(Continued)

*Primary Examiner* — Venkataraman Balasubramanian
(74) *Attorney, Agent, or Firm* — Dilworth IP, LLC

(57) ABSTRACT

The invention relates to a compound for use in treating a cancer, wherein the cancer depends on the proteolytic activity of the MALT1 protease, and wherein the compound has the general formula (I)

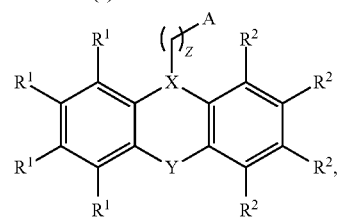

Figure 1:
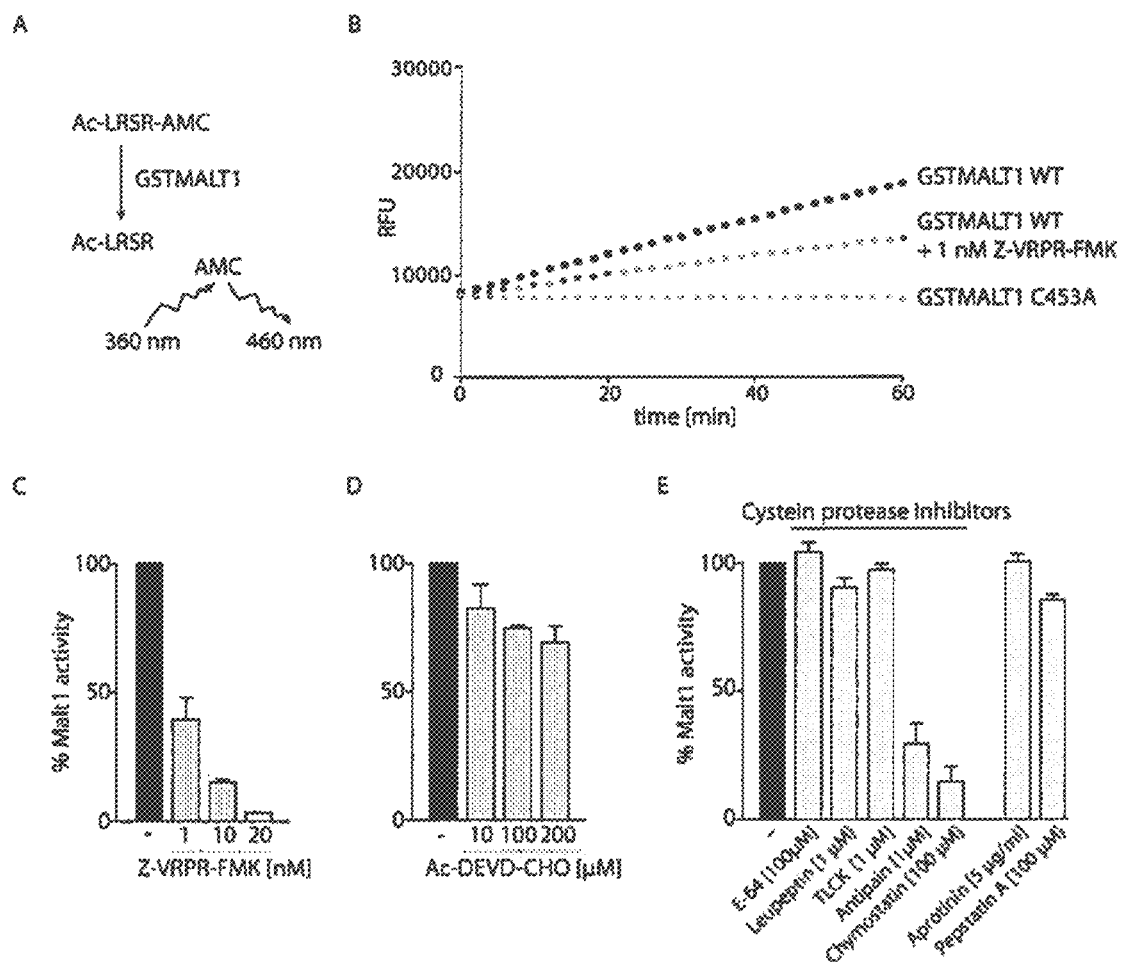

wherein X is N or C; Y is S, O, $SO_2$, SO, NH, CO, $CH_2$, CH=CH, or $CH_2$—$CH_2$; ( )$_z$ is a $C_1$-$C_5$ linear or branched alkyl chain; A is $NR^3R^4$, or $OR^5$, or HET; $R^1$ and $R^2$ in each occurrence are independently selected from —H, —$CH_3$, —OH, —$OCH_3$, —$SCH_3$, —F, —Cl, —$CF_3$, —$NH_2$, and —COOH; $R^3$, $R^4$, and $R^5$ are H, or $C_1$-$C_5$ linear or branched alkyl groups, and HET is a heterocyclic ring of 5, 6, or 7 members, wherein the ring atoms can be C, O, N, or S, the ring can be saturated or aromatic, and the ring can be substituted with H or $C_1$-$C_5$ linear or branched alkyl groups; or a pharmaceutically acceptable salt, prodrug, enantiomer, diastereomer, racemic mixture, crystalline form, amorphous form, unsolvated form or solvate of said compound. The compound of the invention may further be used in the treatment of MALT1-dependent immune diseases.

21 Claims, 17 Drawing Sheets

(56) References Cited

FOREIGN PATENT DOCUMENTS

| | | |
|---|---|---|
| JP | 2009515851 A | 4/2009 |
| JP | 2010502621 A | 1/2010 |
| JP | 2011513319 A | 4/2011 |
| WO | 9605185 A1 | 2/1996 |
| WO | 97/33871 A1 | 9/1997 |
| WO | 02058684 A2 | 8/2002 |
| WO | 03062388 A2 | 7/2003 |
| WO | 2005105145 A1 | 11/2005 |
| WO | 2007054550 A1 | 5/2007 |
| WO | 2008027521 A1 | 3/2008 |
| WO | 2009108635 A2 | 9/2009 |
| WO | 2014207067 | 12/2014 |

OTHER PUBLICATIONS

European Search Report in EP 11006346.8 by applicant company Helmholtz Zentrum München Deutsches Forschungszentrum fur Gesundheit und Umwelt (GmbH), Dec. 28, 2011.

Thome, M., "Multifunctional roles for MALT1 in T•cell activation", Nature Reviews, Immunology, 2008; 8(7), 495-500.

Scheidereit, C., "IkB kinase complexes: gateways to NF-jB activation and transcription", Oncogene, 2006; 25(51), 6685-6705.

Oeckinghaus et al. "Malt1 ubiquitination triggers NF-jB signaling upon T-cell activation", The EMBO Journal, 2007; 26 (22), 4634-4645.

Uren, et al. "Identification of Paracaspases and Metacaspases: Two Ancient Families of Caspase-like Proteins, One of which Plays a Key Role in MALT Lymphoma", Molecular Cell, Oct. 2000, 6(4):961-967.

Vercammen et al. "Protein Synthesis, Post-Translation Modification and Degradation: Type II Metacaspases Atmc4 and Atmc9 of Arabidopsis thaliana Cleave Substrates after Arginine and Lysine", Journal of Biological Chemistry, 2004, 279(44): 45329-45336.

Coornaert et al. "T cell antigen receptor stimulation induces MALT1 paracaspase—mediated cleavage of the NF-jB inhibitor A20", Nature Immunology, 2008; 9(3): 263-271.

Rebeaud et al. "The proteolytic activity of the paracaspase MALT1 is key in T cell activation", Nature Immunology, 2008; 9(3): 272-281.

Staal, et al. "T-cell receptor-induced JNK activation requires proteolytic inactivation of CYLD by MALT1", the EMBO Journal, 2011; 30(9): 1742-1752.

Duwel et al. "A20 Negatively Regulates T Cell Receptor Signaling to NF-B by Cleaving Malt1 Ubiquitin Chains1" The Journal of Immunology, 2009, 182(12): 7718-7728.

Ngo et al. "A loss-of-function RNA interference screen for molecular targets in cancer", Nature, 2006; 441(7089): 106-110.

Allzadeh et al. "Distinct types of diffuse large B-cell lymphoma identified by gene expression profiling", Nature, 2000, 403 (6769): 503-511.

Rosenwald, "Gene Expression Profiling of Diffuse Large B-Cell Lymphoma", Leukemia & Lymphona, 2003; 44, Supplement 3: S41-S47.

Rosenwald, The Use of Molecular Profiling to Predict Survival After Chemotherapy for Diffuse Large-B-Cell Lymphoma, New England Journal of Medicine, 2002; 346(25): 1937-1947.

Savage, et al., "The molecular signature of mediastinal large B-cell lymphoma differs from that of other diffuse large B-cell lymphomas and shares features with classical Hodgkin lymphoma", Blood, 2003; 102(12): 3871.

Wright et al., "A gene expression-based method to diagnose clinically distinct subgroups of diffuse large B cell lymphoma", PNAS, 2003;100(17): 9991-9996.

Staudt et al. The Biology of Human Lymphoid Malignancies Revealed by Gene Expression Profiling, Adv Immunol. 2005; 87: 163-208.

Davis et al. "Constitutive Nuclear Factor B Activity Is Required for Survival of Activated B Cell-like Diffuse Large B Cell Lymphoma Cells", The Journal of Experimental Medicine, 2001; 194(12): 1861-1874.

Lenz et al., "Oncogenic CARD11 Mutations in Human Diffuse Large B Cell Lymphoma", Science, 2008; 319(5870): 1675-1679.

Davis et al., "Chronic active B-cell-receptor signalling in diffuse large B-cell lymphoma", Nature, 2010; 463 (7277): 88-92.

Ferch et al. "Inhibition of MALT1 protease activity is selectively toxic for activated B cell-like diffuse large B cell lymphoma cells" J. Exp. Med, 2009; 206(11): 2313-2320.

Hachmann et al. "Mechanism and specificity of the human paracaspase MALT1", Biochem J., 2012; 443: 287-295.

Isaacson, et al., "MALT lymphoma: from morphology to molecules" Nature Reviews Cancer, 2004, 4(8): 644-653.

Rosenbeck, et al. "Cleavage of NIK by the API2-MALT1 Fusion Oncoprotein Leads to Noncanonical NF-kB Activation", Science, 2011; 331(6016): 468-472.

Vercammen et al. "Serpin1 of Arabidopsis thaliana is a Suicide Inhibitor for Metacaspase 9", J. Mol. Biol. (2006) 364: 625-636.

Whittier et al. "Mepazine (Pacatal): Clinical Trial with Placebo Control and Psychological Study", Psychopharmacologia,1960; 1: 280-287.

Kloo et al., Critical role of PI3K signaling for NF-kB—dependent survival in a subset of activated B-cell-like diffuse large B-cell lymphoma cells, PNAS, 2011;108(1): 272-277.

Su et al., "Requirement for Caspase-8 in NF-kB Activation by Antigen Receptor", Science 2005, 307(5714), 1465-1468.

Choi et al., "Potential Inhibition of PDK1/Akt Signaling by Phenothiazines Suppresses Cancer Cell Proliferation and Survival" Ann. N.Y. Acad. Sci. 2008; 1138: 393-403.

Rho et al., "A gene signature-based approach identifies thioridazine as an inhibitor of phosphatidylinositol-3'-kinase (PI3K)/AKT pathway in ovarian cancer cells", Gynecologic Oncology, 2011; 120(1):121-127.

Seeman et al., "Antipsychotic drug doses and neuroleptic/dopamine receptors" Nature, 1976; 261(5562): 717-719.

Sarwer-Foner et al., "The Clinical Investigation of Pacatal in Open Psychiatric Settings", Canad. M.A.J.; 1957, 77(5): 450-459.

Lord et al. "A Report on Mepazine, A Tranquilizing Drug", Canadian Journal of Comparative Medicine; 1957; 21(11): 391-394.

van Soolingen et al. "The Antipsychotic Thioridazine Shows Promising Therapeutic Activity in a Mouse Model of Multidrug-Resistant Tuberculosis" PloS One, 2010; 5 (9): 1-6.

Weisman et al., "Searching for New Antimalarial Therapeutics amongst Known Drugs" Chem. Biol. Drug Des. 2006; 67 (6): 409-416.

Lisurek et al. "Design of chemical libraries with potentially bioactive molecules applying a maximum common substructure concept" Mol. Divers., 2010;14(2): 401-408.

Yin et al. "Lack of apoE causes alteration of cytokines expression in young mice liver" Mol. Biol. Rep., 2010; 37(4) :2049-2054.

Parsonnet et al. "Helicobacter Pylori Infection and Gastric Lymphoma", N. Engl. J. Med., 1994; 330(18): 1267-1271.

Staal, et al. "Regulation of NF-kB signaling by caspases and MALT1 paracaspase"; Cell Research (2011) 21:40-54.

Hailfinger, et al. "Adapter and enzymatic functions of proteases in T-cell activation", Immunological Review 2009, vol. 232: 334-347.

Jaworski et al. "The paracaspase MALT1: biological function and potential for therapeutic inhibition", Cell. Mol. Life Sci (2016) 73:459-473.

McGuire et al. "Pharamacological inhibition of MALT1 protease activity protects mice in a mouse model of multiple sclerosis", Journal of Neuroinflammation (2014) 11:124.

Chamba, A. et al., Leukemia Research, 2010, vol. 34, pp. 1103-1106.

Meredith, E. J. et al., The FASEB Journal, 2005, vol. 19, No. 9, pp. 1187-1189.

Reynolds, I. J. et al, Journal of Pharmacology and Experimental Therapeutics, 1988, vol. 247, No. 3, pp. 1025-1031.

Baur, E W. et al., Journal of Pharmacology and Experimental Therapeutics, 1971, vol. 177, No. 1, pp. 219-226.

Maurer, H. et al., Journal of Chromatography, 1984, pp. 125-145.

Szabo, W. A. et al., J. Org. Chem., 1980, vol. 45, pp. 744-746.

Hewick, D. S. et al, Biochem. J., 1971, vol. 122, No. 5, pp. 59-60.

Motohashi, N. et al., Anticancer Research, 1996, vol. 16, No. 5A, pp. 2525-2532.

(56) References Cited

OTHER PUBLICATIONS

Afonina, I. et al., "The paracaspase MALT1 mediates CARD14-induced signaling in keratinocytes", EMBO reports, vol. 17, No. 6, pp. 914-927, 2016.

Herrmann, R. et al., Journal of Biomolecular Screening, 2008, vol. 13, No. 1, pp. 1-8.

Nieschulz, O. et al., Arzneimittel-Forschung, 1960, vol. 10, pp. 156-165.

Madrid, P. B. et al., Bioorganic & Medicinal Chemistry Letters, 2007, vol. 17, No. 11, pp. 3014-3017.

Matthews, N. et al., Biochemical Pharmacology, 1995, vol. 50, No. 7, pp. 1053-1061.

Matsuda, K. et al., Arzneimittel Forschung = Drug Research, 1970, vol. 20, No. 10, pp. 1596-1604.

Mayer, M. et al, Chemistry & Biology, 2006, vol. 13, pp. 993-1000.

Bourquin, J.P. et al., Helevitica Chimica Acta, 1959, vol. 42, pp. 259-281.

Barron, D. I. et al., J. Med. Chem., 1963, vol. 6, pp. 705-711.

Japanese Office Action mailed Apr. 11, 2016 from corresponding JP Application No. 2014-523321, along with unofficial English translation.

Howes, A. et al., Psoriasis mutations disrupt CARD14 autoinhibition promoting BCL10-MALT1-dependent NF-κB activation, Biochem J. (2016) 473, 1759-1768.

\* cited by examiner

Figure 3
A
B
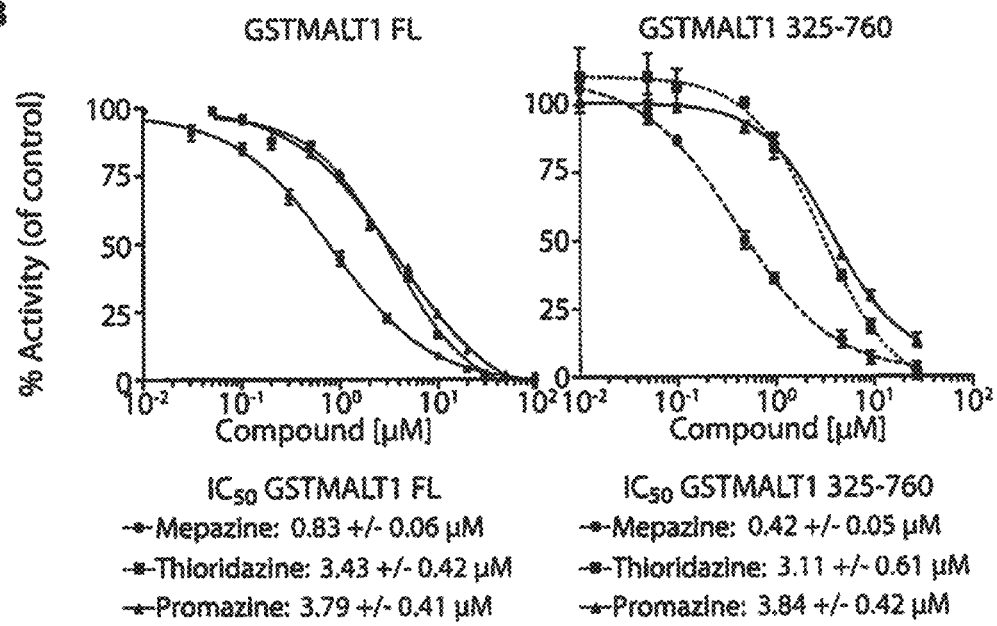
IC$_{50}$ GSTMALT1 FL
- Mepazine: 0.83 +/- 0.06 µM
- Thioridazine: 3.43 +/- 0.42 µM
- Promazine: 3.79 +/- 0.41 µM
IC$_{50}$ GSTMALT1 325-760
- Mepazine: 0.42 +/- 0.05 µM
- Thioridazine: 3.11 +/- 0.61 µM
- Promazine: 3.84 +/- 0.42 µM
C
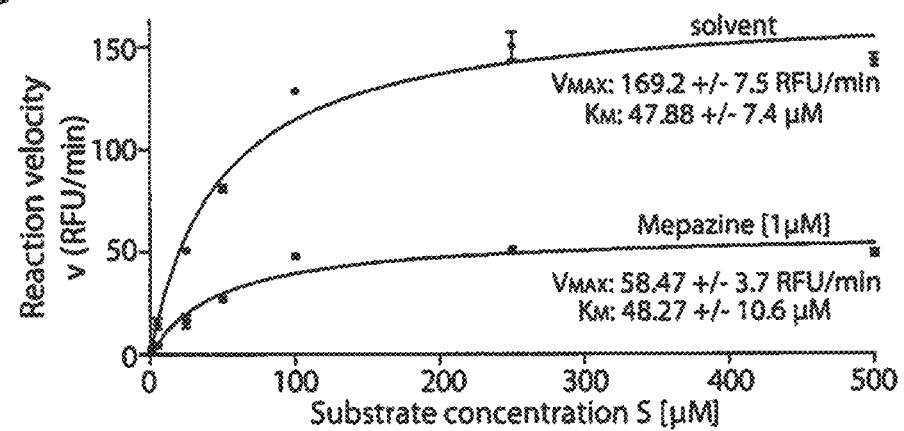
solvent
V$_{MAX}$: 169.2 +/- 7.5 RFU/min
K$_M$: 47.88 +/- 7.4 µM
Mepazine [1µM]
V$_{MAX}$: 58.47 +/- 3.7 RFU/min
K$_M$: 48.27 +/- 10.6 µM Figure 3 – continued
D
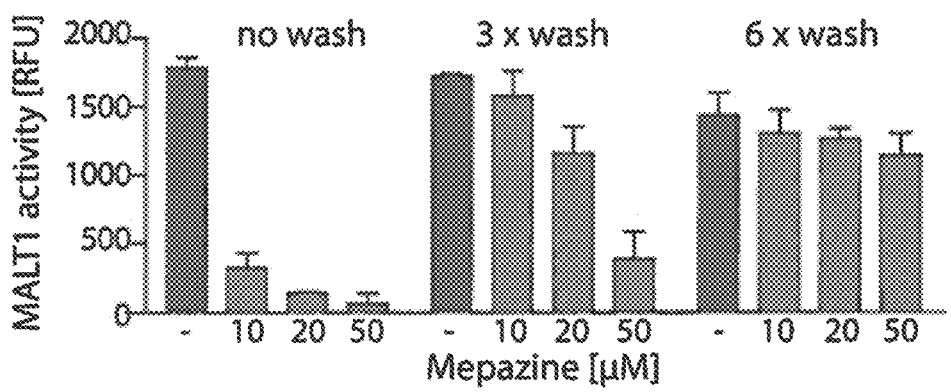
E
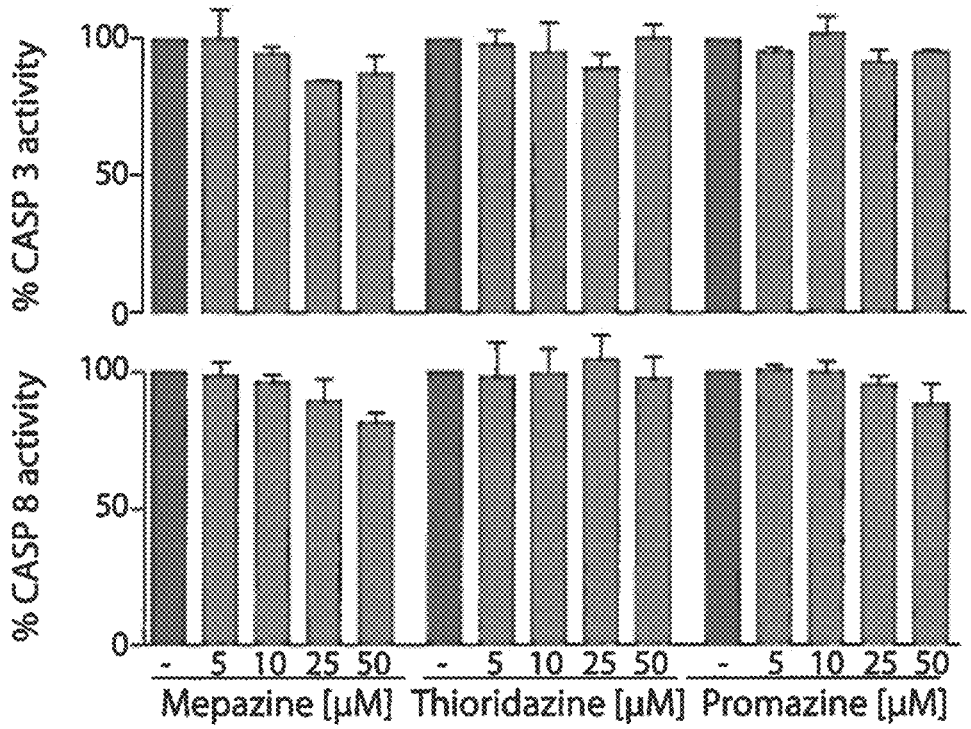

Figure 4
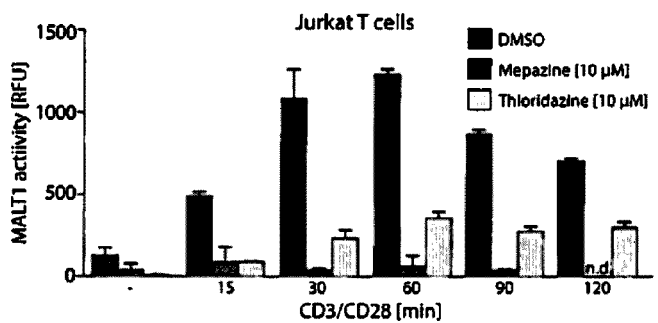
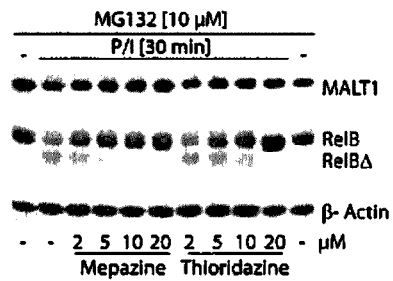
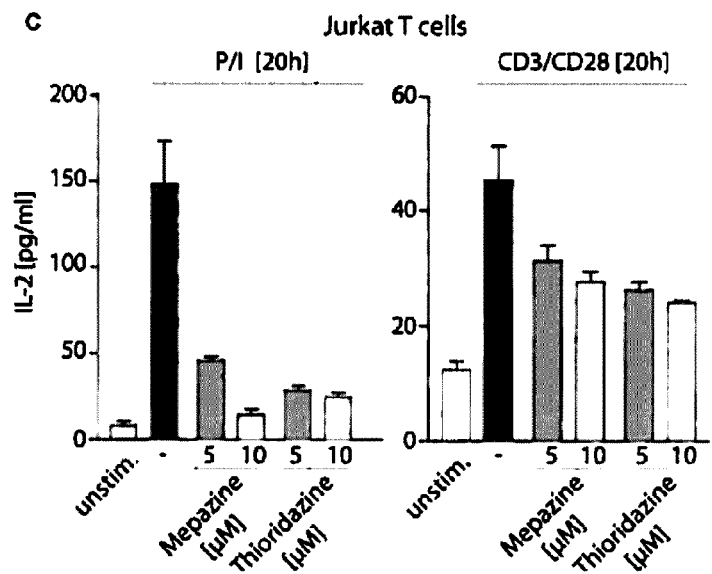

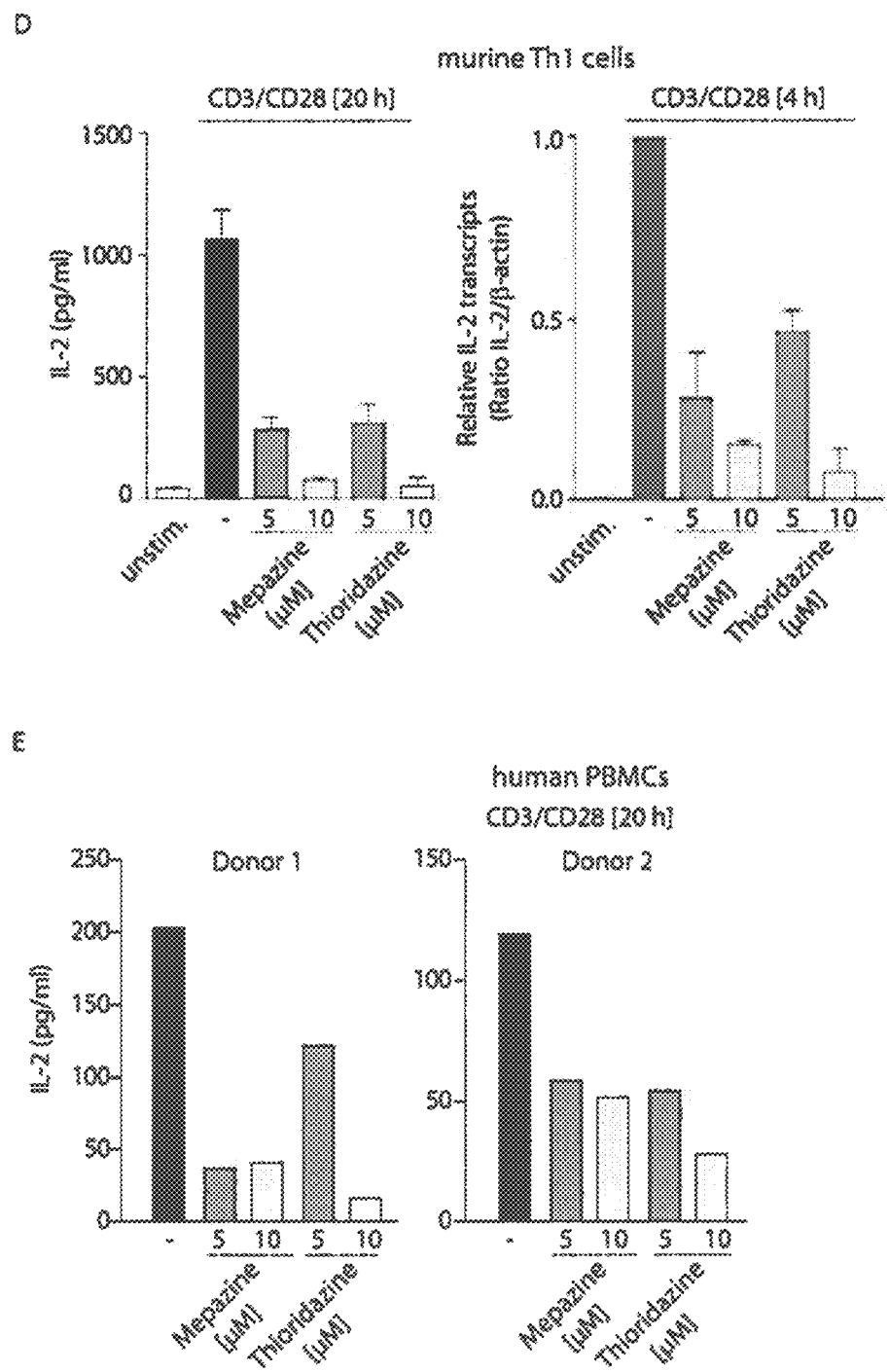

Figure 8
A
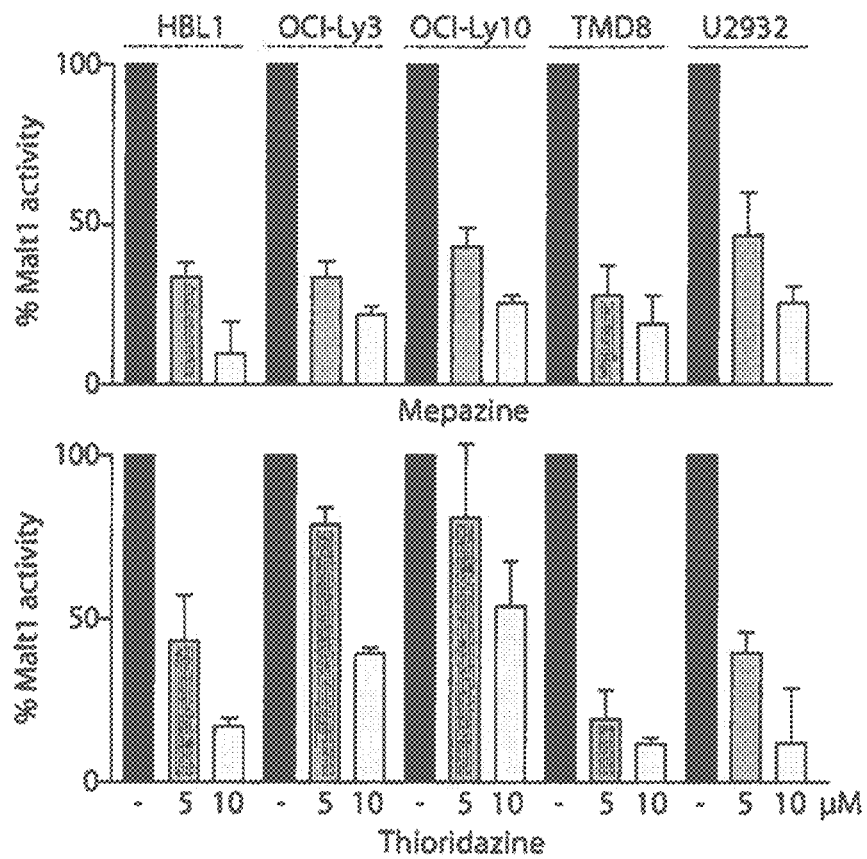
B
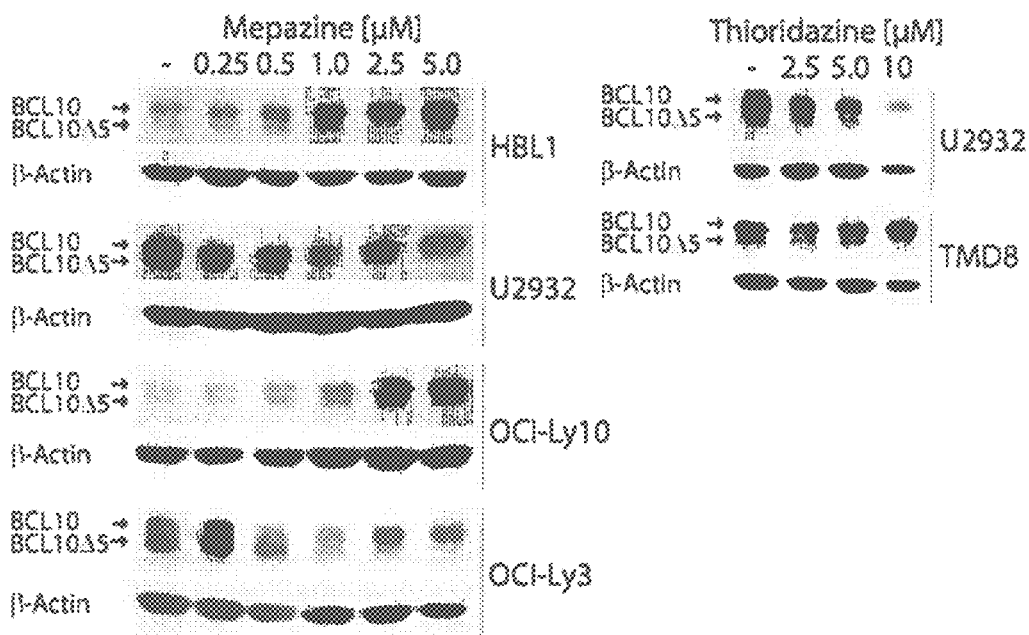

Figure 6
A
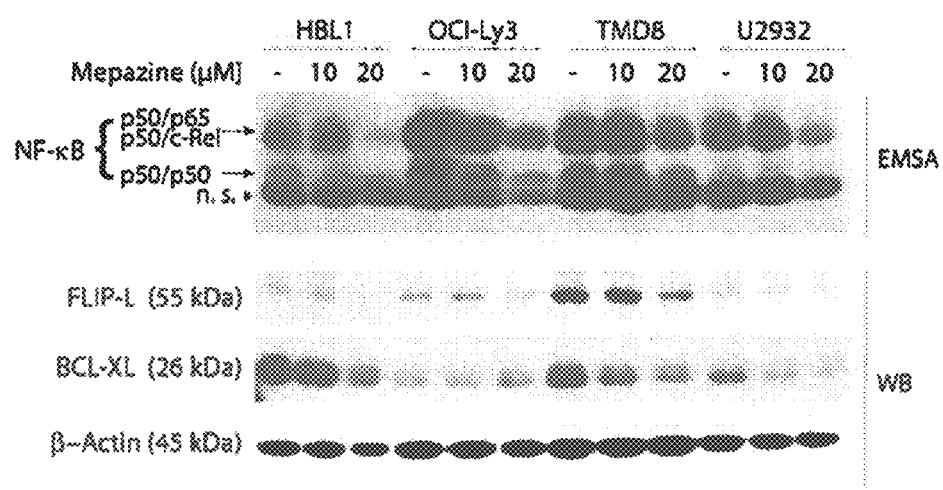
B
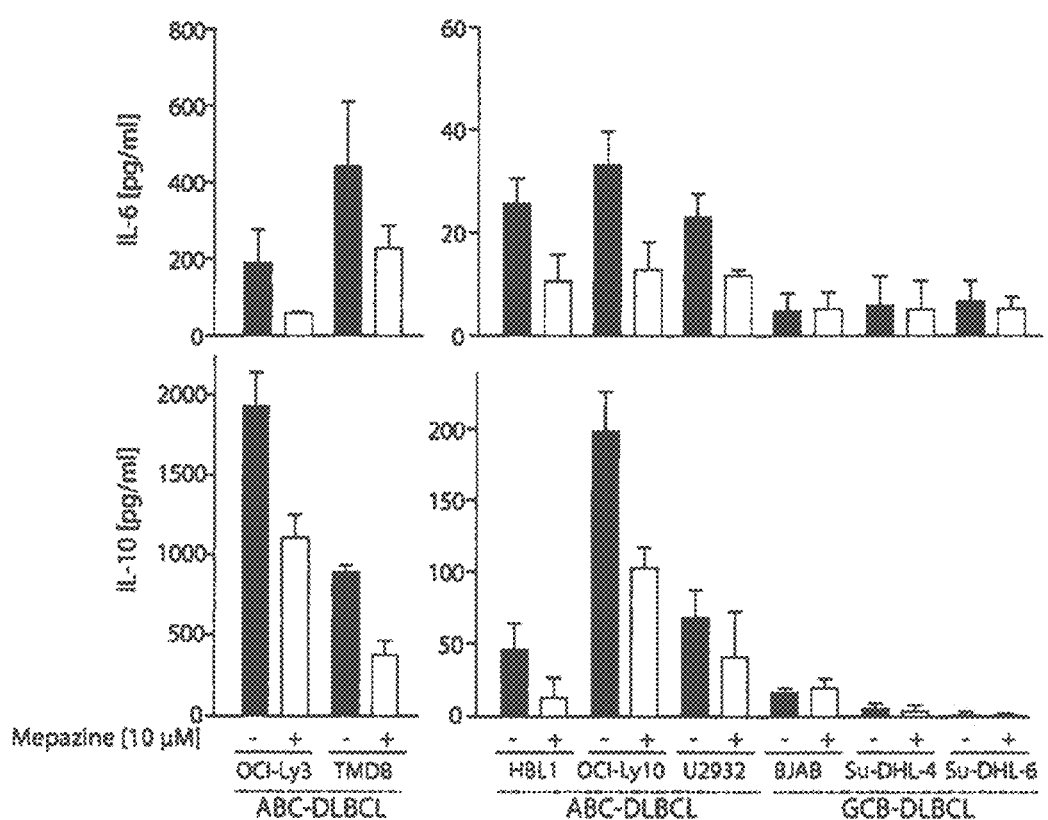

Figure 7
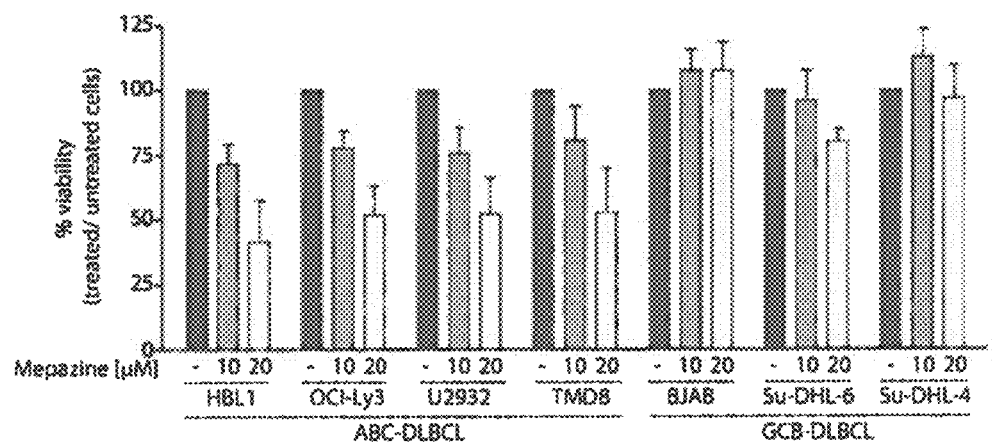
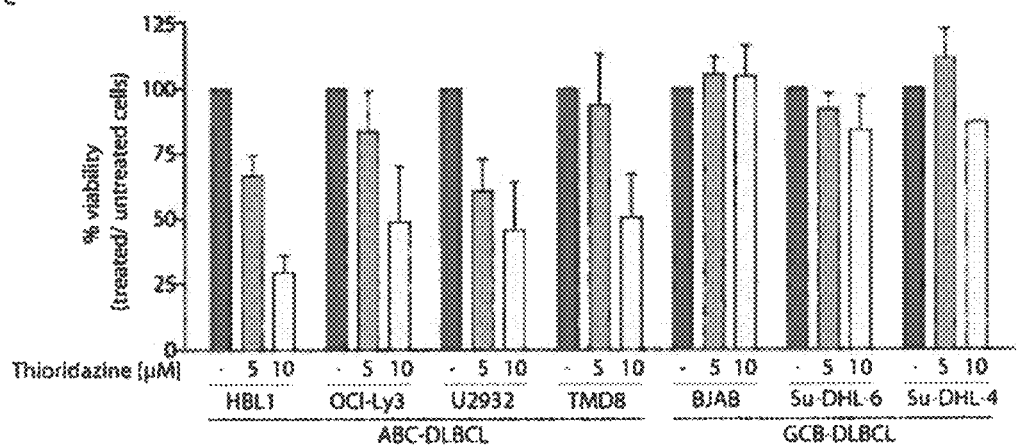
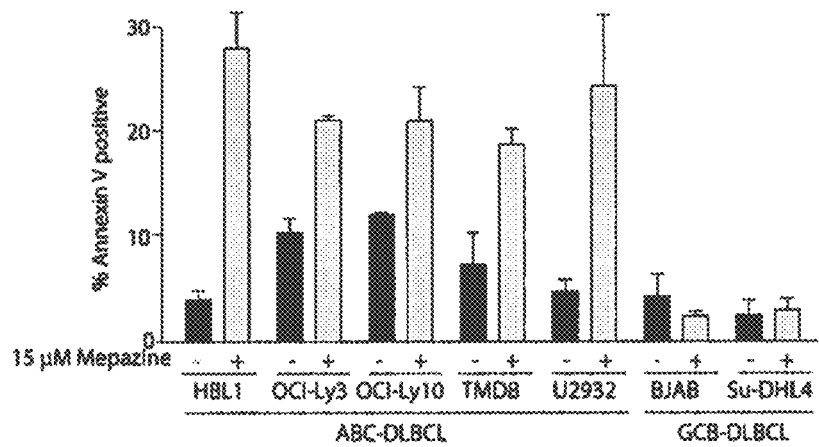

Figure 7 – continued
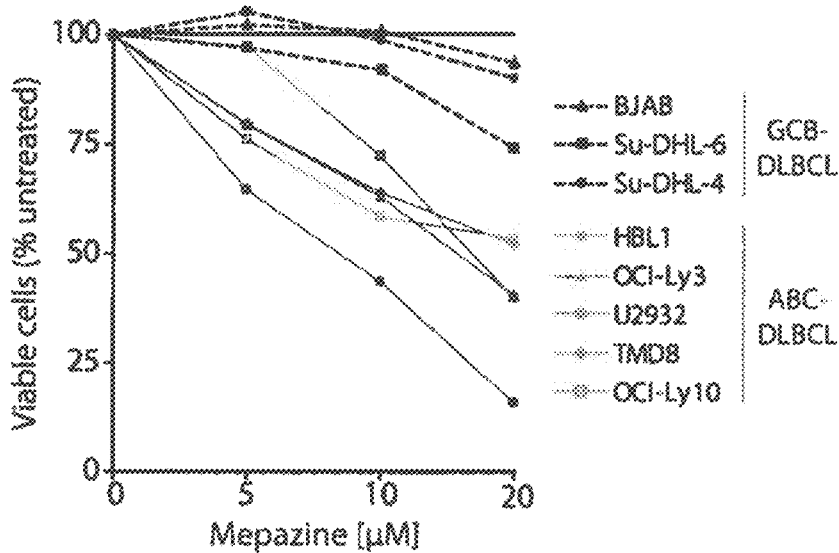
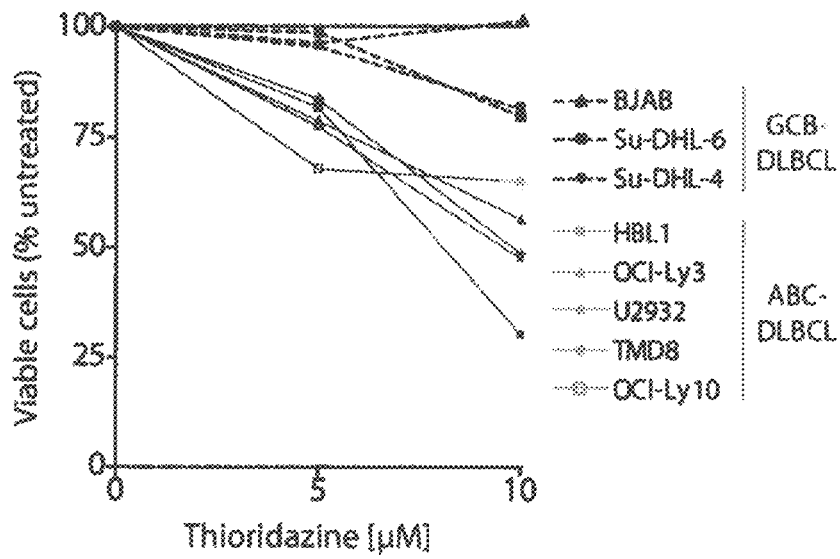

Figure 8
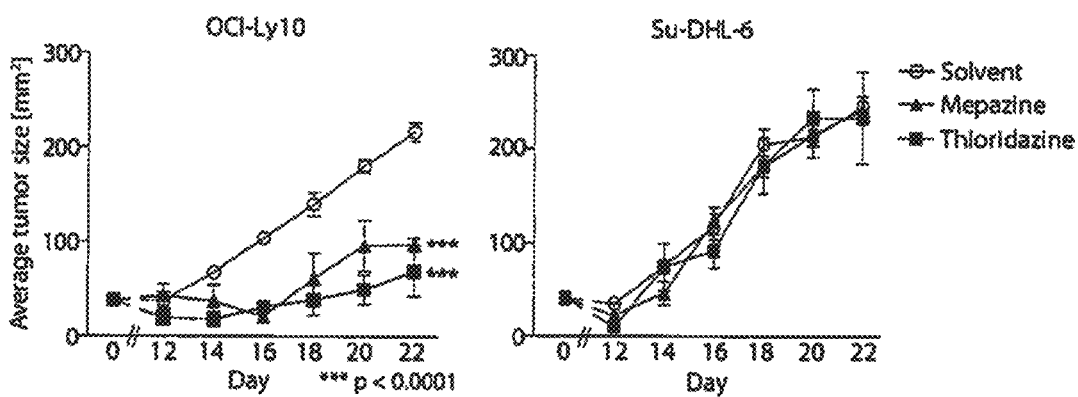
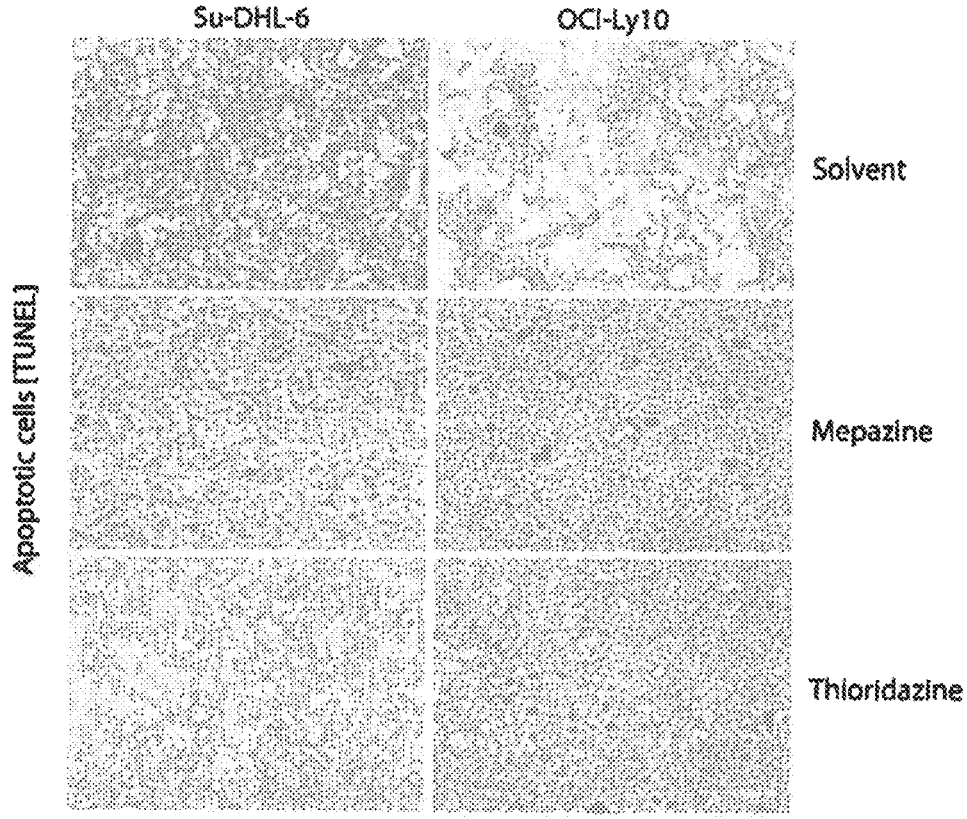
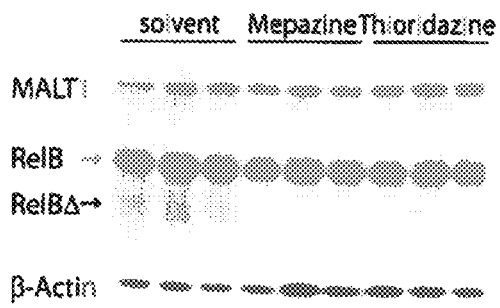

Figure 9

|  | Malt1 | Atmc4* | Atmc9* | |
|---|---|---|---|---|
| Pepstatin [100 μM] | 83 % | 66 % | 69 % | Aspartyl proteases |
| Aprotinin [5 μg/ml] | 100 % | 114 % | 113 % | |
| TLCK [1 μM] | 97 % | 79 % | 0 % | Serin proteases |
| Chymostatin [100 μM] | 10 % | 14 % | 10 % | |
| Leupeptin [1 μM] | 91 % | 12 % | 5 % | Cysteine proteases |
| Antipain [1 μM] | 30 % | 6 % | 1 % | |
| E-64 [100 μM] | 105 % | 44 % | 93 % | |
| Ac-DEVD-CHO [100 μM] | 75 % | n.d. | n.d. | Caspases |
| t-DEVD-cmk [100 μM] | n.d. | 94 % | 94 % | |

*Vercammen et al. 2004

Figure 10

|  | Primary screen | Validation of primary screen |
| --- | --- | --- |
| Compounds | ~ 18,000 | ~ 300 |
| Comp. concentration | 10 µM | 0.7 - 90.9 µM |
| GSTMalt1 conc. | 170 nM | 170 nM |
| Assay volume | 11 µl | 11 µl |
| Assay time | 20 min | 20 min |
| Substrate conc. | 50 µM | 50 µM |
| Microplates | 384 Half-well NBS | 384 Half-well NBS |
| Hits | ~ 300 | 15 |
| % hits of library | 1.67 % | 0.08 % |

Figure 11
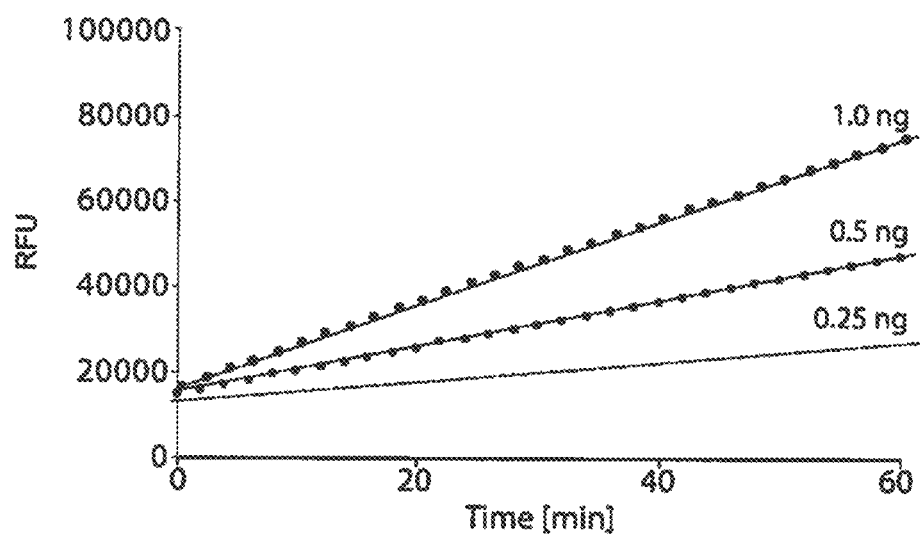
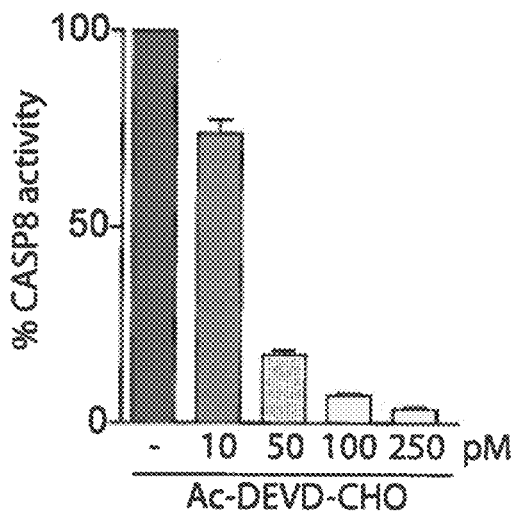

Figure 12:
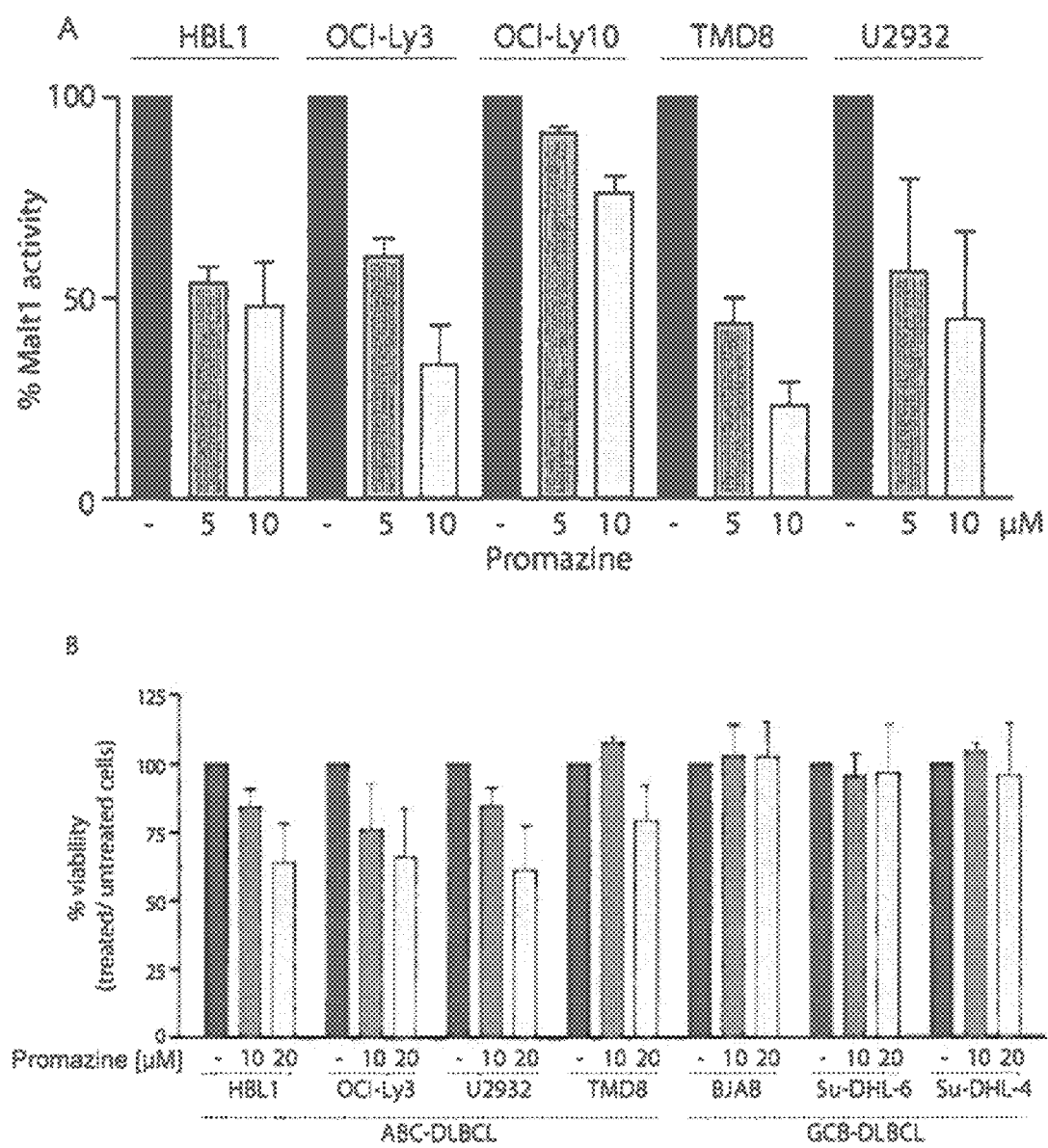

Figure 12 – continued
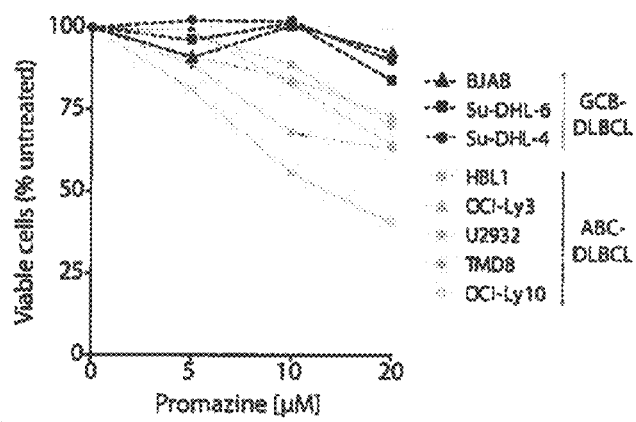
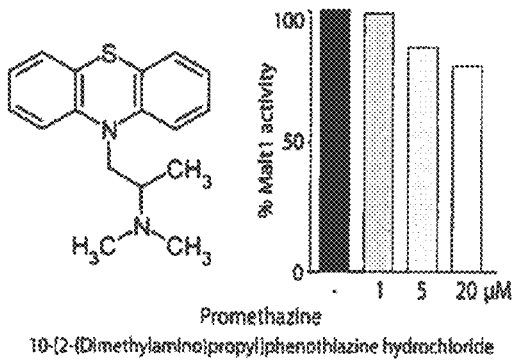
Promethazine
10-[2-(Dimethylamino)propyl]phenothiazine hydrochloride
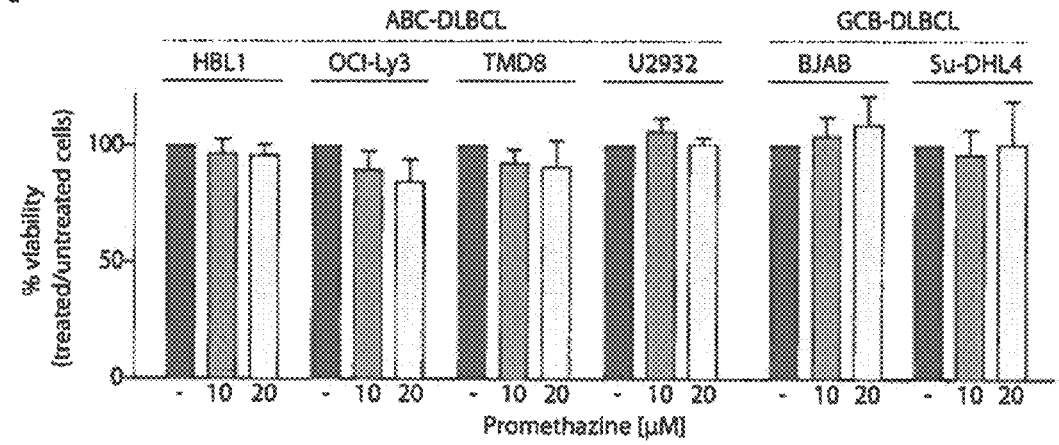

SELECTIVE INHIBITION OF MALT1 PROTEASE BY PHENOTHIAZINE DERIVATIVES

This application is a U.S. National Phase Application under 35 U.S.C. §371 of International Patent Application No. PCT/EP2012/065072, filed on Aug. 1, 2012, which claims priority to European Patent Application No. EP 11006346.8, filed on Aug. 2, 2011, the disclosures of each of which are incorporated herein by reference in their entirety.

The invention relates to a compound for use in treating a cancer, wherein the cancer depends on the proteolytic activity of the MALT1 protease, and wherein the compound has the general formula (I)

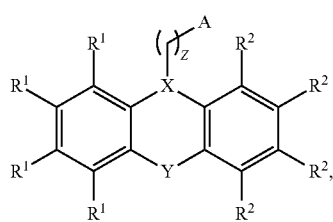

wherein X is N or C; Y is S, O, $SO_2$, SO, NH, CO, $CH_2$, CH=CH, or $CH_2$—$CH_2$; ( )$_z$ is a $C_1$-$C_5$ linear or branched alkyl chain; A is $NR^3R^4$, or $OR^5$, or HET; $R^1$ and $R^2$ in each occurrence are independently selected from —H, —$CH_3$, —OH, —$OCH_3$, —$SCH_3$, —F, —Cl, —$CF_3$, —$NH_2$, and —COOH; $R^3$, $R^4$, and $R^5$ are H, or $C_1$-$C_5$ linear or branched alkyl groups, and HET is a heterocyclic ring of 5, 6, or 7 members, wherein the ring atoms can be C, O, N, or S, the ring can be saturated or aromatic, and the ring can be substituted with H or $C_1$-$C_5$ linear or branched alkyl groups; or a pharmaceutically acceptable salt, prodrug, enantiomer, diastereomer, racemic mixture, crystalline form, amorphous form, unsolvated form or solvate of said compound. The compound of the invention may further be used in the treatment of MALT1-dependent immune diseases.

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The mucosa-associated lymphoid tissue lymphoma translocation protein 1 (MALT1) is a functional cysteine protease activated by T-cell receptor stimulation. MALT1 rapidly cleaves A20 (TNFAIP) after arg439, which impairs its NF-κB inhibitor function (Coornaert et al. (2008), Nature Immun. 9: 263-271).

Upon antigenic stimulation, MALT1 is a key mediator of upstream NF-κB signaling to control lymphocyte activation, survival and differentiation.[1] Together with CARMA1 (also known as CARD11) and BCL10, MALT1 assembles the so called CBM complex that bridges proximal antigen receptor signaling events to the IκB kinase (IKK) complex, the gatekeeper of the canonical NF-κB pathway.[2] Upon T cell antigen receptor (TCR)/CD28 co-stimulation, MALT1 acts as a protein scaffold that recruits other critical signaling molecules like TRAF6, CASP8 and A20 to the CBM complex.[1] Further, covalent ubiquitin modifications in MALT1 catalyzed by the E3 ligase TRAF6 facilitates the association of the two downstream protein kinase complexes TAB2-TAK1 and NEMO-IKKα/β, which ultimately leads to IKK activation.[3]

MALT1 contains a paracaspase domain that displays high homology to caspases from mammals and metacaspases from plants and fungi.[4] Just like metacaspases, MALT1 cleaves substrates after arginine residues, indicating that the enzymatic cleavage activity is quite distinct from caspases that in general require an aspartate at the P1 position.[5] MALT1 proteolytic activity is induced upon TCR/CD28 stimulation, which promotes cleavage of the substrates BCL10, A20 and CYLD.[6-8] Inhibition of MALT1 protease activity by the antagonistic tetra-peptide Z-VRPR-FMK that was originally designed as an inhibitor of metacaspases in plants impairs optimal NF-κB activation and IL-2 production in T cells.[7,9] Similar, mutation of the catalytic cysteine 464 renders MALT1 proteolytically inactive and also impairs IL-2 production after complementation of MALT1 deficient T cells.[9]

Disregulation of the activity of the MALT1 protease plays a crucial role in the development of a number of diseases, in particular cancers that depend on the proteolytic activity of the MALT1 protease and MALT1-dependent immune diseases. A tumor-promoting role of MALT1 has been found in a subset of diffuse-large B cell lymphomas (DLBCL) and mucosa-associated lymphatic tissue (MALT) lymphomas.[10] By gene expression profiling, DLBCL can be classified into distinct entities and the most abundant subtypes are the 'activated B cell-like' (ABC-) DLBCL and the 'germinal center B cell-like' (GCB-) DLBCL.[11-15] Based on the gene expression signature the ABC-DLBCL subtype originates from B-lymphocytes stimulated through their B cell antigen receptor (BCR). With a 5-year survival rate of ~30% ABC-DLBCL patients have the worst prognosis reflecting the aggressive clinical behavior of ABC-DLBCL cells.[16] The hallmark of ABC-, but not GCB-DLBCL cells, is the constitutive activation of the NF-κB signaling pathway.[11,17] The identification of distinct molecular aberrations suggested that pro-survival NF-κB signaling in ABC-DLBCL is caused by deregulations in BCR signaling. While some ABC-DLBCL patients carry oncogenic CARMA1 mutations,[18] the majority of ABC-DLBCL cells is characterized by chronic active BCR signaling and mutations are often found in the BCR proximal regulator CD79A and B.[19] Congruent with a requirement on BCR signaling, an RNA interference screen identified CARMA1, BCL10 or MALT1 as critical regulators of NF-κB activation, survival and growth of ABC-DLBCL.[10] Furthermore, inhibition of MALT1 proteolytic activity by Z-VRPR-FMK inhibits NF-κB dependent gene expression and exerts toxic effects specifically in ABC-DLBCL cells.[20,21] Ferch et al. (2009), J. Exp. Med. 206: 2313-2320 showed that aggressive activated B cell-like (ABC) diffuse large B cell lymphoma (DLBCL) cells, but not germinal center B cell-like (GCB) DLBCL, possess constitutively assembled CARD11-BCL10-MALT1 (CBM) complexes that continuously and selectively process A20. Inhibition of MALT1 blocks A20 and BCL10 cleavage, reduces NFκB activity, and decreases the expression of NF-κB targets BCLXL (BCL2L1), IL6, and IL10. Inhibition of MALT1 paracaspase leads to ABC-DLBCL cell death and growth retardation. Ferch et al. (2009) concluded that MALT1 paracaspase activity has a growth-promoting role, specifically in ABC-DLBCL cells, and proposed that MALT1 protease activity is a potential target for pharmacologic treatment of ABC-DLBCL.

MALT lymphoma is a cancer of the B-cell lymphocytes. It usually affects older people who are in their 60s. Most Non-Hodgkin Lymphomas (NHLs) start in the lymph nodes, but MALT lymphoma starts in a type of lymphatic tissue called mucosa-associated lymphoid tissue (MALT). The stomach is the most common area for MALT lymphoma to develop in, but it may also start in other organs such as the lung, thyroid, salivary gland or bowel. Because MALT lymphoma develops outside the lymph nodes, its also known as extranodal lymphoma. Gastric MALT lymphoma is frequently associated (72-98%) with chronic inflammation as a result of the presence of *Helicobacter pylori* (Parsonnet J (1994). N Engl J Med 330 (18): 1267-71). The initial diagnosis is made by biopsy of suspicious lesions on esophagogastroduodenoscopy (EGD, upper endoscopy). Simultaneous tests for *H. pylori* are also done to detect the presence of this microbe. In other sites, chronic immune stimulation is also suspected in the pathogenesis (e.g. association between chronic autoimmune diseases such as Sjögren's syndrome and Hashimoto's thyroiditis, and MALT lymphoma of the salivary gland and the thyroid). In MALT lymphoma the frequent translocation t(11;18)(q21;q21) creates a fusion between the C-terminus of MALT1 including the paracaspase domain and the N-terminus of IAP2.[22] The paracaspase domain of IAP2-MALT1 fusion protein catalyzes the cleavage of NIK and thereby enhances non-canonical NF-κB activation, which confers apoptosis resistance.[23]

Taken together novel agents against the MALT1 paracaspase could be beneficial for the treatment of lymphoma associated with deregulated MALT1 activity and MALT1-dependent immune diseases. In particular, the overall five year survival rate of only ~30% of ABC-DLBCL patients emphasizes the clear need for alternative treatment options, in particular for this lymphoma type.[16] Thus, an object of the present invention is the provision of novel agents against MALT1 which can be used in the treatment of the above-discussed diseases.

Accordingly the invention relates in a first embodiment to a compound for use in treating a cancer, wherein the cancer depends on the proteolytic activity of the MALT1 protease, and wherein the compound has the general formula (I)

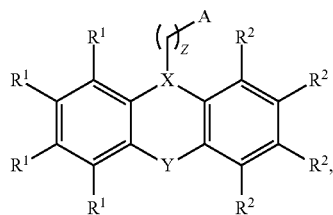

wherein X is N or C; Y is S, O, $SO_2$, SO, NH, CO, $CH_2$, CH=CH, or $CH_2$-$CH_2$; $(\ )_z$ is a $C_1$-$C_5$ linear or branched alkyl chain; A is $NR^3R^4$, or $OR^5$, or HET; $R^1$ and $R^2$ in each occurrence are independently selected from —H, —$CH_3$, —OH, —$OCH_3$, —$SCH_3$, —F, —Cl, —$CF_3$, —$NH_2$, and —COOH; $R^3$, $R^4$, and $R^5$ are H, or $C_1$-$C_5$ linear or branched alkyl groups, and HET is a heterocyclic ring of 5, 6, or 7 members, wherein the ring atoms can be C, O, N, or S, the ring can be saturated or aromatic, and the ring can be substituted with H or $C_1$-$C_5$ linear or branched alkyl groups; or a pharmaceutically acceptable salt, prodrug, enantiomer, diastereomer, racemic mixture, crystalline form, amorphous form, unsolvated form or solvate of said compound.

The term "a cancer that depends on the proteolytic activity of the MALT1 protease" as used herein defines a cancer which is partly or predominately caused by unphysiologically elevated (proteolytic) activity of MALT1. The enzymatic activity of MALT-1 comprises a cystein protease activity (EC 3.4.22.—cysteine endopeptidases). As it is evident from the appended examples, the inventors have found that the compounds of the invention specifically inhibit the activity of MALT1. As discussed herein above in detail, MALT1 activity is responsible for optimal NF-κB activation and IL-2 production in antigen receptor-stimulated T cells. This indicates that MALT1 activity is essential for the physiological lymphocyte activation. Accordingly, a cancer that depends on the proteolytic activity of the MALT1 protease is preferably a lymphoma that depends on the proteolytic activity of the MALT1 protease. Preferred examples of lymphomas that depend on the proteolytic activity of the MALT1 protease are the activated B-cell subtype (ABC-subtype) of the diffuse-large B cell lymphoma and the MALT lymphoma which are discussed in more detail herein below.

Also encompassed by the present invention are pharmaceutically acceptable salts, prodrugs, enantiomers, diastereomers, racemic mixtures, crystalline forms, non-crystalline forms, amorphous forms, unsolvated forms and solvates compound of the general formula (I).

The term "pharmaceutically acceptable salts" as used herein includes salts of the compound of the general formula (I) which are prepared with relatively nontoxic (i.e. pharmaceutically acceptable) acids or bases, depending on the particular substituents found on the compounds of the present invention. If, for example, compounds of the present invention contain acidic functionalities, base addition salts may be obtained by contacting the neutral form of such compounds with a sufficient amount of the desired base, either neat or in a suitable inert solvent. Non-limiting examples of pharmaceutically acceptable base addition salts include sodium, potassium, calcium, ammonium, organic amino, or magnesium salt, or a similar salt. If compounds of the present invention contain basic functionalities, acid addition salts may be obtained by contacting the neutral form of such compounds with a sufficient amount of the desired acid, either neat or in a suitable inert solvent. Non-limiting examples of pharmaceutically acceptable acid addition salts include those derived from inorganic acids like hydrochloric, hydrobromic, nitric, carbonic, phosphoric, partially neutralized phosphoric acids, sulfuric, partially neutralized sulfuric, hydroiodic, or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present invention may contain both basic and acidic functionalities that allow the compounds to be converted into either base or acid addition salts. The neutral forms of the compounds of the present invention may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

The compounds of the present invention may possess chiral or asymmetric carbon atoms (optical centers) and/or double bonds. The racemates, diastereomers, geometric isomers and individual optical isomers are encompassed by the present invention. The compounds of the present invention may exist in unsolvated forms as well as solvated forms, including hydrated forms. In general, the solvated forms are equivalent to unsolvated forms and are also encompassed by the present invention. The compounds of the present invention may furthermore exist in multiple crystalline or amorphous forms.

In addition to salt forms, the compounds of the present invention may be in a prodrug form. Prodrugs of the compounds of the invention are those compounds that readily undergo chemical changes under physiological conditions to provide the compounds of the present invention. Additionally, prodrugs can be converted to the compounds of the present invention by chemical or biochemical methods in an ex-vivo environment. For example, prodrugs can be slowly converted to the compounds of the present invention when, for example, placed in a transdermal patch reservoir with a suitable enzyme or chemical reagent.

The compound of the invention described herein can be administered to the subject at a suitable dose. The compound of the invention is preferably administered to mammals such as domestic and pet animals. Non-limiting examples of domestic and pet animals are pigs, cows, buffalos, sheep, goats, rabbits, horses, donkeys, chickens, ducks, cats, dogs, genuine pigs, or hamsters. Most preferred it is administered to humans. The preferred way of administration depends on the form of the compound of the invention (having the general formula (I)). As described herein above, the compound having the general formula (I) can be in the form of pharmaceutically acceptable salts, prodrugs, enantiomers, diastereomers, racemic mixtures, crystalline forms, non-crystalline forms, amorphous forms, unsolvated forms or solvates. The compound of the invention may be administered orally, parenterally, such as subcutaneously, intravenously, intramuscularly, intraperitoneally, intrathecally, transdermally, transmucosally, subdurally, locally or topically via iontophoresis, sublingually, by inhalation spray, aerosol or rectally and the like in dosage unit formulations optionally further comprising conventional pharmaceutically acceptable excipients.

The compound of the invention for use in accordance with the present invention can be formulated as a pharmaceutical composition using one or more physiological carriers or excipient, see, for example Ansel et al., "Pharmaceutical Dosage Forms and Drug Delivery Systems", 7th edition, Lippincott Williams & Wilkins Publishers, 1999.

For oral administration, the pharmaceutical composition of the invention can take the form of, for example, tablets or capsules prepared by conventional means with pharmaceutical acceptable excipients such as binding agents (e.g., pregelatinised maize starch, polyvinylpyrrolidone, hydroxypropyl methylcellulose), fillers (e.g., lactose, microcrystalline cellulose, calcium hydrogen phosphate), lubricants (e.g., magnesium stearate, talc, silica), disintegrants (e.g., potato starch, sodium starch glycolate), or wetting agents (e.g., sodium lauryl sulphate). The pharmaceutical composition can be administered with a physiologically acceptable carrier to a patient. In a specific embodiment, the term "pharmaceutically acceptable" means approved by a regulatory agency or other generally recognized pharmacopoeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium ion, dried skim milk, glycerol, propylene, glycol, water, ethanol and the like. The composition, if desired, can also contain minor amounts of wetting or emulsifying agents, or pH buffering agents. These compositions can be in the form of ointments, solutions, suspensions, emulsion, tablets, pills, capsules, powders, sustained-release formulations and the like. A preferred form is an ointment. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E.W. Martin. Such compositions will contain a therapeutically effective amount of the aforementioned compounds, preferably in purified form, together with a suitable amount of carrier so as to provide the form for proper administration to the patient. The formulation should suit the mode of administration.

Liquid preparations for oral administration can be in the form of, for example, solutions, syrups, or suspensions, or can be presented as a dry product for constitution with water or other suitable vehicle before use. Such liquid preparation can be prepared by conventional means with pharmaceutically acceptable additives such as suspending agents (e.g., sorbitol, syrup, cellulose derivatives, hydrogenated edible fats), emulsifying agents (e.g., lecithin, acacia), non-aqueous vehicles (e.g., almond oil, oily esters, ethyl alcohol, fractionated vegetable oils), preservatives (e.g., methyl or propyl-p-hydroxycarbonates, soric acids). The preparations can also contain buffer salts, flavouring, coloring and sweetening agents as deemed appropriate. Preparations for oral administration can be suitably formulated to give controlled release of the pharmaceutical composition of the invention.

For administration by inhalation, the pharmaceutical composition of the invention is conveniently delivered in the form of an aerosol spray presentation from a pressurised pack or a nebulizer, with the use of a suitable propellant (e.g., dichlorodifluoromethane, trichlorofluoromethane, dichlorotetrafluoroethane, carbon dioxide or other suitable gas). In the case of a pressurised aerosol, the dosage unit can be determined by providing a valve to deliver a metered amount. Capsules and cartridges of, for example, gelatine, for use in an inhaler or insufflator can be formulated containing a powder mix of the pharmaceutical composition of the invention and a suitable powder base such as lactose or starch.

The pharmaceutical composition of the invention can be formulated for parenteral administration by injection, for example, by bolus injection or continuous infusion. Site of injections include intra-venous, intra-peritoneal or sub-cutaneous. Formulations for injection can be presented in units dosage form (e.g., in phial, in multi-dose container), and with an added preservative. The pharmaceutical composition of the invention can take such forms as suspensions, solutions or emulsions in oily or aqueous vehicles, and can contain formulatory agents such as suspending, stabilizing, or dispersing agents. Alternatively, the agent can be in powder form for constitution with a suitable vehicle (e.g., sterile pyrogen-free water) before use. Typically, compositions for intravenous administration are solutions in sterile isotonic aqueous buffer. Where necessary, the composition can also include a solubilizing agent and a local anesthetic such as lignocaine to ease pain at the site of the injection. Generally, the ingredients are supplied either separately or mixed together in unit dosage form, for example, as a dry lyophilised powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

The pharmaceutical composition of the invention can also, if desired, be presented in a pack, or dispenser device which can contain one or more unit dosage forms containing the said agent. The pack can for example comprise metal or plastic foil, such as blister pack. The pack or dispenser device can be accompanied with instruction for administration.

The pharmaceutical composition of the invention can be administered as sole active agent or can be administered in combination with other agents.

In accordance with the first embodiment it is preferred that X is N. Moreover, it is preferred that Y is S. $(\ )_z$ is preferably a linear $C_1$-$C_5$ alkyl chain, and more preferably a linear $C_1$-$C_3$ alkyl chain. $R^1$ is preferably —H; and $R^2$ is preferably —H or —$SCH_3$. Preferably, the preferred embodiments can be present independent of one another. In a further preferred embodiment the features of all preferred embodiments are present.

Thus, according to a preferred embodiment the compound for use according to the invention has the above formula (I), wherein in formula (I) X is N; Y is S; $(\ )_z$ is a linear $C_1$-$C_5$ alkyl chain, $R^1$ is —H; and $R^2$ is —H or —$SCH_3$.

In accordance with a more preferred embodiment of the invention the compound for use according to the invention has the above formula (I), wherein in formula (I) A is HET and HET is a 5-membered to 7-membered carbocyclic ring which is optionally interrupted with $NR^3$.

In this regard it is preferred that HET is a 6-membered carbocyclic ring. It is even more preferred that HET is a 6-membered carbocyclic ring which is interrupted with $NR^3$, wherein $R^3$ is $CH_3$.

In accordance with a further more preferred embodiment of the invention the compound for use according to the invention has the above formula (I), wherein in formula (I) A is $NR^3R^4$ and $R^3$ is H or $CH_3$ and $R^4$ is —$CH_3$.

In this regard it is most preferred that $R^3$ and $R^4$ are —$CH_3$.

In accordance with another more preferred embodiment of the invention the compound for use according to the invention has the above formula (I), wherein in formula (I) A is $NR^3R^4$, wherein $R^3$ is $CH_3$, $R^4$ is —$CH_3$, —$C_2H_5$, or a C3-C5 linear alkyl chain the chain of which may be interrupted by O, N or S and which forms a saturated ring with a carbon atom of $(\ )_z$. In this regard it is most preferred that $R^4$ is —$CH_3$.

In accordance with an even more preferred embodiment of the invention the compound for use according to the invention has the above formula (I), wherein the saturated ring is a 5-membered to 7-membered carbocyclicring which is interrupted with N.

In this regard it is preferred that the 5-membered to 7-membered alkylene ring which is optionally interrupted with N is a 6-membered alkylene ring. It is also preferred that the saturated ring is a 5-membered to 7-membered saturated carbocyclic ring (not interrupted with N) and more preferably a 6-membered saturated carbocyclic ring (not interrupted with N).

In accordance with a more preferred embodiment of the invention the compound for use according to the invention has the above formula (I), wherein in formula (I) A is HET and HET is N-Methylpiperidin-3-yl.

In accordance with a further more preferred embodiment of the invention the compound for use according to the invention has the above formula (I), wherein in formula (I) (a) Z=3 and A is $NR^3R^4$ and $R^3$ and $R^4$ are —$CH_3$, (b) Z=1 and A is N-methylpiperidin-3-yl; or (c) Z=2 and A is N-methylpiperidin-2-yl.

In accordance with the most preferred embodiment of the invention, the compound for use according to the invention is

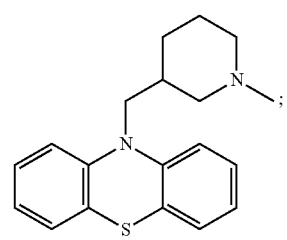

Formula (II)

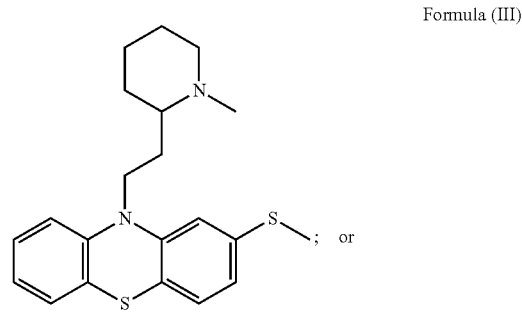

Formula (III)

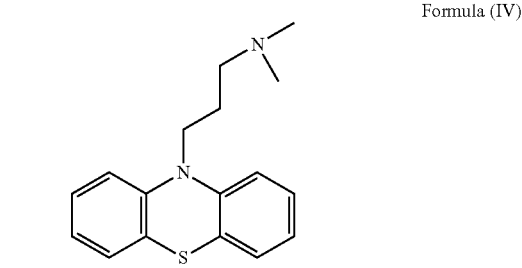

Formula (IV)

The compound of formula (II) is known in the art as Mepazine. Mepazine is a phenothiazine which was initially used as a tranquilizer (Lord and Archibald (1957), Can J Comp Med Vet Sci., 21(11): 391-394).

The compound of formula (III) is known in the art as Thioridazine. Thioridazine also belongs to the phenothiazine drug group. Thioridazine is know in the art as antipsychotic drug and was widely used in the treatment of schizophrenia and psychosis.

The compound of formula (IV) is known in the art as Promazine. Promazine is a derivative of phenothiazine. Promazine is used in the art as antipsychotic drug, e.g., to treat schizophrenia.

All three phenothiazine derivatives (PDs) analyzed in the appended examples have been in clinical trials and used as antipsychotic and/or sedative drugs and this activity is thought to primarily base on their ability to function as dopamine D2 receptor antagonists.[30] Mepazine has been evaluated as an antipsychotic and tranquilizing drug under the brand name Pacatal in the late 50s and early 60s. Whereas some clinical investigations have attested an antipsychotic effect, others failed to do so.[25,31] Some side effects were reported, including a reduction of asthma attacks after Mepazine treatment indicating a certain immunosuppressing activity.[31] To the best knowledge of the inventors, no observations concerning potential beneficial effects on cancer patients have been reported. Neither study design nor cohort sizes allow to draw any conclusion that Mepazine, Thioridazine and Promazine may specifically inhibit MALT1. Thioridazine (brand name Mellaril) is still commercially available, but prescription is reserved to the treatment of schizophrenic patients, who do not respond to other antipsychotic drugs. Thioridazine is also considered to be beneficial for other medical applications, as it exerts toxic effects on different cancer cell lines.[29,32] However, the inventors are not aware of any prior art which shows or indicates that Thioridazine exerts toxic effects on a cancer cell line which depends on the proteolytic MALT1 activity. In addition, Thioridazine is considered as a candidate drug for the treatment of tuberculosis or malaria, but the reason for its anti-microbial and anti-parasitic action is currently unknown.[33,34] Promazine (brand name Sparine), which displayed the weakest toxicity on MALT1 dependent ABC-DLBCL, is still used to treat restless behavior.

Thus, the compounds of formula (II), (Ill) and (IV) were all initially used in the art as antipsychotic drug. In the appended examples Mepazine, Thioridazine and Promazine were identified as three small molecule inhibitors of MALT1. To the best knowledge of the inventors none of these compounds was know to inhibit the activity of MALT1 protease. The results illustrated in the examples of the invention show for the first time that the compounds of formula (II), (Ill) and (IV) can be used to treat a cancer that depends on the proteolytic activity of the MALT1 protease.

In accordance with a preferred embodiment of the invention, the cancer that depends on the proteolytic activity of the MALT1 protease is the activated B-cell subtype of diffuse-large B cell lymphoma or MALT lymphoma.

As it has been described herein above, diffuse large B-cell lymphoma (DLBCL) is a type of aggressive lymphoma. One major subtype of DLBCL which has been identified based on its genetic activity is the B-cell subtype of diffuse-large B cell lymphoma (ABC-DLBCL). As it has been described herein above, Ferch et al. (2009), J. Exp. Med. 2006: 2313-2320 showed that aggressive activated B cell-like (ABC) diffuse large B cell lymphoma (DLBCL) cells possess constitutively assembled CARD11-BCL10-MALT1 (CBM) complexes that continuously and selectively process A20. Moreover, inhibition of MALT1 paracaspase leads to ABC-DLBCL cell death and growth retardation. Thus, the examples herein below which show that the phenothiazines derivatives Mepazine, Thioridazine and Promazine specifically inhibit MALT1 indicate for the first time that ABC-DLBL can be treated by using the compound of the invention.

As it has been described herein above, MALT lymphoma is a cancer of the B-cell lymphocytes. Most NHLs start in the lymph nodes, but MALT lymphoma starts in mucosa-associated lymphoid tissue (MALT). MALT lymphomas usually start in areas of the body where there has been an infection or when the person has an autoimmune condition affecting that area. Most cases of MALT lymphoma affecting the stomach are linked to infection by a bacteria called *Helicobacter pylori*. In other sites, chronic immune stimulation is also suspected in the pathogenesis (e.g. association between chronic autoimmune diseases such as Sjögren's syndrome and Hashimoto's thyroiditis, and MALT lymphoma of the salivary gland and the thyroid). Three translocation associated with MALT lymphoma have been identified; namely t(11;18)(q21;q21), giving rise to a API2-MLT fusion gene, t(1;14)(p22;q32) which deregulates BCL10, and t(14;18) (q32;q21), which deregulates MALT1. All three translocations are believed to turn-on the same pathway, i.e. the pathway of API2-MALT. Thus, the examples herein below which show that the phenothiazine derivatives Mepazine, Thioridazine and Promazine specifically inhibit MALT1 indicate for the first time that MALT lymphoma can be treated by using the compound of the invention.

In accordance with the present invention phenothiazine derivatives (PDs) have been identified as the first class of small molecule inhibitors that effectively and selectively inhibit proteolytic activity of recombinant and cellular MALT1 protease. As it can be taken from the examples, the best inhibitory activity was obtained with mepazine, thioridazine and promazine. All three PDs are shown to interfere with inducible or constitutive MALT1 activity from activated T cells or from ABC-DLBCL cells, respectively. Furthermore, these PDs cause an impaired T cell activation as well as reduced viability selectively of the ABC subtype of DLBCL cells, processes that have been shown to critically depend on MALT1 activity.[9,20,21] Thus, the cellular data further evidence the effectiveness of PDs as pharmacological MALT1 inhibitors.

Different assay conditions were initially tested and the effects of broad spectrum protease inhibitors to characterize cleavage activity of recombinant full length MALT1 in more detail. Interestingly, the proteolytic activity of MALT1 resembled *Arabidopsis thaliana* metacaspases AtMC4 and 9,[5] emphasizing that the structural homology between paracaspase and metacaspase domains is causing similar substrate binding and cleavage properties. As MALT1 is the only human paracaspase with very distinct properties when compared to other human caspases, specific inhibitors as defined in accordance with the present invention are clearly promising candidates for selective inactivation of its oncogenic activity. Selectivity is critical, as impairing the execution of apoptosis by the inhibition of caspases other than MALT1 would likely trigger adverse effects that could not be tolerated for lymphoma therapy. Indeed, all PDs tested display a high preference for MALT1 and are not acting on the initiator caspase CASP8 and the executioner caspase CASP3. Furthermore, as CASP8 associates with MALT1 and is required for NF-κB signaling in T cells,[27] the apparent lack of CASP8 inhibition by PDs also underscores the requirement for proteolytic MALT1 activity to trigger optimal T cell activation. The strong inhibition of cellular MALT1 activity even after relatively short PD incubation clearly indicates that the substances directly affect the MALT1 protease.

In addition, the inhibitory action of the MALT1 inhibitory compounds of the invention on T cell activation indicates a potential medical use as mild immunosuppressants for instance in the treatment of allergy and asthma.

Accordingly, also encompassed by the present invention is a compound of the invention for use in the treatment of MALT1-dependent immune diseases.

In accordance with a preferred embodiment thereof, the MALT1-dependent immune disease is an allergic inflammation.

Also described herein is a method of treating a cancer that depends on proteolytic activity of the MALT1 protease in a subject, comprising administering a pharmaceutically effective amount of a compound of the invention to the subject. In this regard, the cancer that depends on proteolytic activity of the MALT1 protease is preferably the activated B-cell subtype of diffuse-large B cell lymphoma or MALT lymphoma. Moreover, the subject is preferably a mammal and more preferably a human.

Furthermore described herein is a method of treating a MALT1-dependent immune disease in a subject, comprising administering a pharmaceutically effective amount of a compound of the invention to the subject. In this regard, the MALT1-dependent immune disease is preferably an allergic inflammation. The MALT1-dependent immune disease also may be a T-cell driven disease where the T-cell responses are counteracted by the compounds such as in Example 5. In this regard MALT1-dependent immune diseases can be hypersensitivity of the immune system or a chronic inflammation such as allergy (as mentioned) or asthma. Further, MALT1-dependent immune disease can be an autoimmune disease, which include but are not limited to diseases such as multiple sclerosis, inflammatory bowel diseases (e.g. Crohn's disease, ulcerative colitis), lupus erythematosus, psoriasis, chronic obstructive pulmonary disease, rheumatoid arthritis or psoriatic arthritis. Moreover, the subject is preferably a mammal and more preferably a human.

The preferred embodiments described herein above also apply to the methods of treatment described herein.

The Figures show:

FIG. 1: Establishment of the in vitro MALT1 cleavage assay for High Throughput Screening (HTS). (A) Scheme of the MALT1 protease assay. Release of the fluorophore AMC by proteolytic action of GSTMALT1 against the fluorogenic peptide Ac-LRSR-AMC containing the BCL10 derived MALT1 cleavage site results in an increase of fluorescence. (B) Kinetics of the MALT1 cleavage reaction. Purified recombinant GSTMALT1 from bacterial expression was incubated for 1 h at 30° C. with 50 µM of Ac-LRSR-AMC and the proteolytic activity was determined by measuring the increase of AMC fluorescence. Whereas the catalytic inactive MALT1 C453A failed to cleave the substrate, inhibition with 1 nM of the inhibitory peptide Z-VRPR-FMK, led to a ~50% decrease of MALT1 activity. (C) MALT1 is inhibited by Z-VRPR-FMK. Increasing amounts of the peptide led to a total loss of MALT1 activity. For evaluation of the data the relative fluorescence of the untreated control was set to 100% and the values of inhibitor treated wells were calculated accordingly. (D) The pan-caspase inhibitor Ac-DEVD-CHO was not significantly active on MALT1 even at 200 µM. (E) Enzymatic characterisation of the MALT1 paracaspase using different protease inhibitors. MALT1 activity was diminished by common concentrations of the cysteine protease inhibitors Antipain (1 µM) and Chymostatin (100 µM), but not by high concentrations of E-64 (100 µM) or a low concentration of Leupetin (1 µM). The aspartyl-protease inhibitor Pepstatin A (100 µM), the serine protease inhibitor Aprotinin (5 µg/ml) and the serine/cysteine protease inhibitor TLCK (1 µM) had no effects on MALT1 activity. The inhibitory profile was compared to the *Arabidopsis* metacaspases AtMC4 and AtMC9 (see FIG. 9). Graphs are showing the mean of at least three independent experiments and error bars indicate SD.

Figure 2:
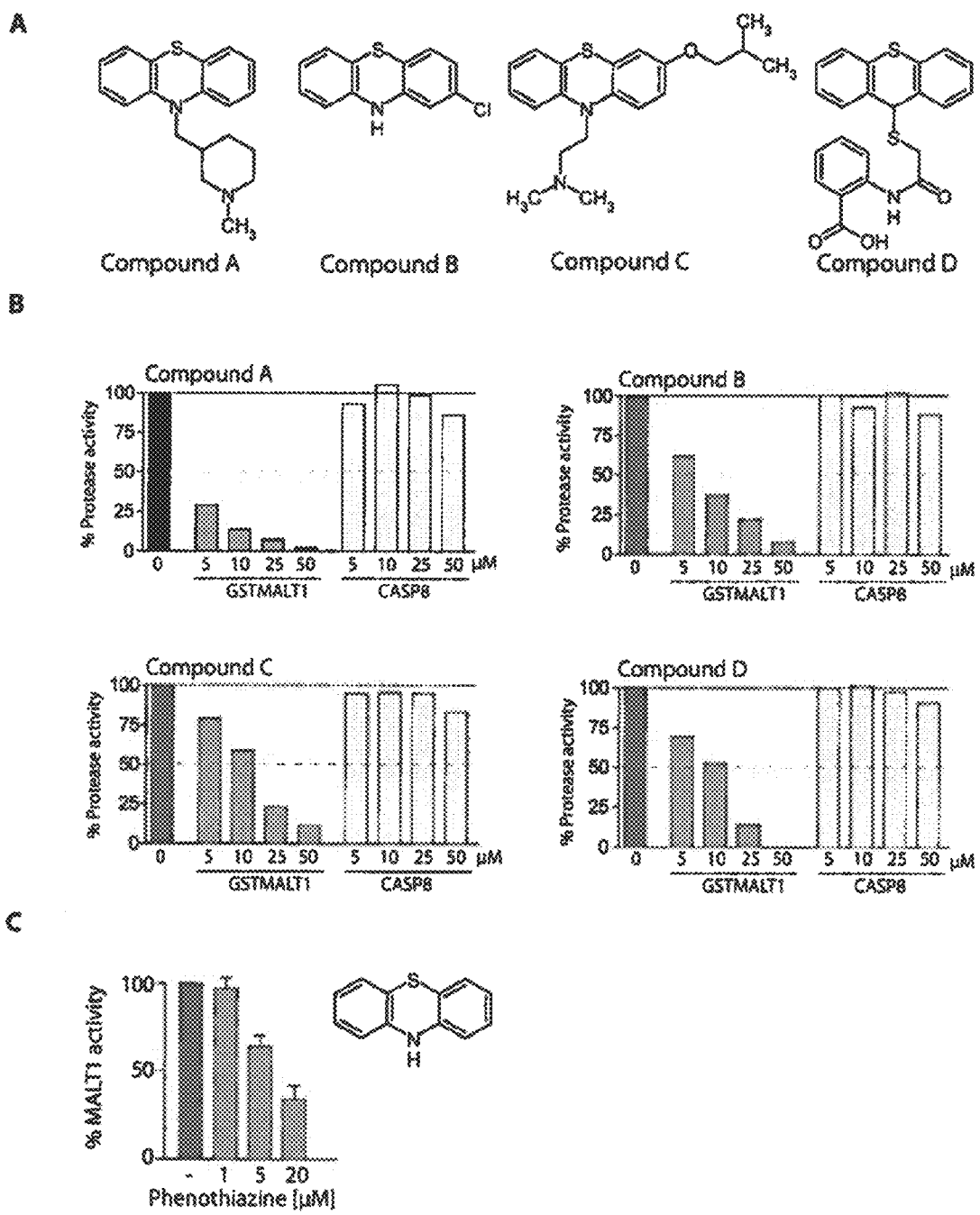

FIG. 2: Phenothiazine derivatives identified by HTS inhibit MALT1 activity. (A) Chemical structures of PDs identified as potential MALT1 inhibitors. Compound A (mepazine; 10-[(1-methyl-3-piperidinyl)methyl]-10H-phenothiazine acetate), B (2-Chlorophenothiazine) and C([2-(3-isobutoxy-10H-phenothiazin-10-yl)ethyl]dimethylamine) being phenothiazine derivatives (PDs) and compound D a structural PD relative. (B) While treatment with increasing amounts of PD from 5 to 50 µM led to a dose-dependent decline of GSTMALT1 activity, enzymatic CASP8 action was not significantly reduced. (C) Inhibition of GSTMALT1 activity with 1, 5 and 20 µM of phenothiazine in a dose-dependent manner. Graphs (in B) are showing one representative of two or the mean of at least three independent experiments (in C) and error bars indicate SD.

FIG. 3: Selective MALT1 inhibition of mepazine, thioridazine and promazine. (A) Molecular structures of the three inhibitory compounds. All three bear a short hydrophobic side chain at the nitrogen with a similar atomic composition and spacing. (B) Dose response curves and IC50 values for mepazine, thioridazine and promazine. (C) Mepazine acts as a non-competitive MALT1 inhibitor. Michaelis-Menten kinetics was determined by increasing concentration of LRSR-AMC substrate in the absence or presence of 1 µM mepazine. Mepazine reduces the $V_{MAX}$ but not the $K_M$ of MALT1. (D) Mepazine acts as a reversible MALT1 inhibitor. GSTMALT1 coupled to Glutathione sepharose beads was treated with mepazine (10, 20 or 50 µM) for 30 min. MALT1 activity was assayed after washing the beads for 0, 3 or 6 times before cleavage reaction was started. (E) PD are selective MALT1 inhibitors and fail to significantly inhibit CASP3 and 8 activity up to concentrations of 50 µM. Data represent the average of at least three independent experiments and error bars indicate SD.

FIG. 4: Mepazine and thioridazine mediated inhibition of MALT1 leading to impaired T cell activation in primary mouse CD4[+] T cells, human PBMCs and Jurkat T cells. (A) Jurkat T cells were left untreated or incubated for 3 h with 10 µM of mepazine or thioridazine and then left unstimulated or stimulated for 15, 30, 60, 90 and 120 minutes with anti-CD3/CD28. Addition of mepazine and thioridazine led to a strong decrease in the activation of cellular MALT1 activity. (B) Treatment of Jurkat T cells with mepazine and thioridazine prevented stimulus and MALT1 dependent cleavage of RelB in a dose-dependent manner. Jurkat T cells were treated with either solvent or 2, 5, 10 or 20 µM of mepazine or thioridazine for 4 h and 1 h MG132 to stabilize RelB cleavage fragment (RelBΔ). Cells were stimulated with P/I for 30 min. RelB and RelBΔ were analyzed by Western Blot. Blots show a representative of at least three independent experiments. (C) To analyze the inhibitory impact of the PD on T cell activation the IL-2 secretion of Jurkat T cells was measured by ELISA after P/I or anti-CD3/CD28 stimulation for 20 h in the presence or absence of 5 and 10 µM mepazine or thioridazine. Both compounds lead to diminished extracellular IL-2 levels after T cell activation. (D) Impact of PD compounds on the activation of primary murine CD4[+] T-cells. Quantitative PCR was used to determine IL-2 mRNA levels after 3 h pre-treatment with mepazine or thioridazine and induction with anti-CD3/

CD28 for 4 h. IL-2 mRNA levels were significantly reduced in compound treated cells compared to solvent treated control cells. In consequence, treatment of the cells with both compounds and subsequent T cell activation with anti-CD3/CD28 antibodies for 20 h resulted in lower levels of secreted IL-2. Graphs (in B-D) are showing the mean of at least three independent experiments. Error bars indicate SD. (E) Primary human PBMCs from two donors were subjected to 5 and 10 µM of mepazine and thioridazine for 3 h before induction with anti-CD3/CD28 for 20 h. In all donors the extracellular IL-2 levels are dose-dependently reduced in the presence of both compounds.

FIG. 5: PD treatment impairs MALT1 activity and a subsequent substrate cleavage in ABC-DLBCL cells. (A) Cellular MALT1 activity in DLBCL was analyzed after 4 h incubation with mepazine and thioridazine. MALT1 was isolated via antibody-based precipitation and its proteolytic activity was determined in a plate reader detecting the flourescence emission of released AMC fluorophors. Both compounds inhibited MALT1 protease activity from ABC-DLBCL cells in a dose-dependent manner with variations depending on the cell line or PD. Graphs are showing the mean of at least three independent experiments and error bars indicate SD (B) Treatment of DLBCL cells with mepazine and thioridazine could prevent the constitutive MALT1 dependent cleavage of BCL10 in a dose-dependent manner. Cells were treated with different doses of compounds for 20 h and the presence of BCL10 and the cleavage product BCL10Δ5 was analyzed via Western Blot. Data are representative of at least three independent experiments.

FIG. 6: Mepazine treatment impairs NF-κB target gene binding and expression in ABC-DLBCL cells. (A) ABC-DLBCL cells were treated with 10 and 20 µM of mepazine for 20 h and subsequently analyzed for NF-κB DNA binding by EMSA. In all four cell-lines NF-κB target gene binding was impaired. Treatment with mepazine consequently decreased the protein levels of the anti-apoptotic NF-κB targets BCL-XL and c-FLIP-L Data are representative of three independent experiments (B) To determine the effect on NF-κB target gene expression, ABC- and GCB-DLBCL control cells were treated with mepazine for 20 h and the levels of the constitutively secreted cytokines IL-6 and IL-10 were analyzed via ELISA. Treatment of the cells resulted in a ~50% decreased IL-6 and IL-10 secretion in ABC cell lines. To account for the drastic variations in cellular IL-6 and IL-10 secretion in the individual cell lines, IL amounts are illustrated with two different scales. Graphs are showing the mean of at least three independent experiments and error bars indicate SD.

FIG. 7: PDs are selectively toxic to ABC-DLBCL cells. (A) to (D) To test the effect of the PDs on the viability of ABC-DLBCL cells four different ABC cell lines and the three GCB-DLBCL cell lines BJAB, Su-DHL-6 and Su-DHL-4 as control cells were treated with indicated concentrations of mepazine or thioridazine (single treatment). Viability of the cells was subsequently analyzed after two days with a MTT cytotoxicity test (A and C) or after four days by cell-counting (B and D). Both compounds could promote a decrease in cell-viability in ABC-DLBCL cell lines, without significantly affecting GCB-DLBCL cells. (E) Analysis of apoptosis in ABC-DLBCL cell lines after mepazine treatment. Five ABC-DLBCL and two GCB-DLBCL cell lines were treated for five days with 15 µM mepazine. Apoptotic cells were identified by FACS analysis as AnnexinV-PE positive and 7-AAD negative cells. While apoptosis was not increased in GCB-DLBCL control cell-lines, an increment of the apoptotic cell population ranging from 10% to 25% was detected in all ABC-DLBCL cell lines. Data (in B and D) are the mean from three independent experiments. Graphs (in A, C and E) are showing the mean of at least three independent experiments and error bars indicate SD.

FIG. 8: Mepazine and thioridazine interfere with growth and induce apoptosis in ABC-DLBCL cell line OCI-Ly10 in vivo. (A) Transplantation of OCI-Ly10 or Su-DHL-6 cells resuspended in matrigel (BD) into the flanks of NOD.Cg-Prkdc$^{scid}$ Il2rg$^{tm1Wjl}$/SzJ (NSG) mice was carried out on day 0. Tumor size was determined by caliper measurement. Intraperitoneal administration of solvent, mepazine (300 µg/d) or thioridazine (400 µg/d) into 3 respective mice of each group was started 24 h after transplantation and given continuously every 24 h for the entire treatment period. Both PD selectively impair growth of the ABC-DLBCL cell line OCI-Ly10. Statistical analysis was performed using a two-way anova test resulting in highly significant p values being <0.0001 from day 16 to 22. (B) Phenothiazines enhance apoptosis in OCI-Ly10, but not Su-DHL-6 cells in vivo. Apoptosis was determined on tumor sections by TUNEL staining after 22 days of treatment. Pictures show staining of representative tumor sections. (C) Mepazine and thioridazine inhibit RelB cleavage in OCI-Ly10 tumors. Expression of RelB and the MALT1-dependent cleavage product RelBΔ were detected in extracts of OCI-Ly10 tumor specimens by Western Blotting after 22 days. Blot shows results from mice treated with solvent, mepazine or thioridazine, displaying three independent samples for each.

FIG. 9: Inhibitory profile of MALT1 implies a high similarity to *Arabidopsis* metacaspases. Similar to AtMC4 and AtMC9 neither 100 µM of the aspartyl protease inhibitor Pepstatin A nor the serine protease inhibitor Aprotinin (5 µg/ml) could inhibit MALT1 proteolytic activity. Chymostatin (100 µM) and Antipain (1 µM) could strongly inhibit MALT1 and the metacaspases, Leupeptin (1 µM) had a stronger effect on AtMC4/9 and whereas the cysteine protease inhibitor E-64 does not inhibit MALT1, it had mild effects on both metacaspases. While TLCK (1 µM) had a slight impact on metacaspases, MALT1 activity was not affected. High doses (100 µM) of DEVD tetra-peptide caspase inhibitors did not inhibit MALT1 or AtMC4/9.

FIG. 10: Parameters for MALT1 HTS. In the primary screen ~18.000 small molecules of the ChemBioNet diversity library were tested with a final concentration of 10 µM against 170 nM of GSTMALT1 in a 384 well format. The resulting 300 hits with the best inhibitory potential were further validated in secondary assays using different doses from 5 to 50 µM. 15 secondary hits were identified corresponding to ~0.08% of the original library.

FIG. 11: (A) Establishment of the proteolytic CASP8 assay. Different amounts of active recombinant CASP8 (0.25, 0.5 and 1 µg) were tested with 50 µM of the caspase substrate Ac-DEVD-AMC. Enzymatic activity was determined in accordance to the GSTMALT1 assay. To analyze the inhibitory impact of PDs on CASP8 250 pg was used. Data is representative of two independent experiments (B) CASP8 activity against Ac-DEVD-AMC in the presence Ac-DEVD-CHO resulted in an almost total decline of enzymatic activity at a concentration of 50 pM. Graphs show the mean of three independent experiments. Error bars indicate SD.

FIG. 12: (A) Promazine inhibits cellular MALT1 activity. Constitutive MALT1 activity in ABC-DLBCL is reduced after 4 h promazine treatment of the cells. (B) and (C) Promazine impairs ABC-DLBCL cell viability. Consistent with the results obtained in the cellular MALT1 cleavage assay, promazine had the mildest effects on ABC-DLBCL cell viability. (D) and (E) The Malt1 non-active Promethazine is not affecting ABC-DLBCL viability. ABC- and GCB-DLBCL cell lines were treated for 4 days with 10 and 20 µM of promethazine, which did not significantly impair viability of both DLBCL subgroups. Data is the mean of three independent experiments. Error bars (in A, B and D) indicate SD.

Figure 13:
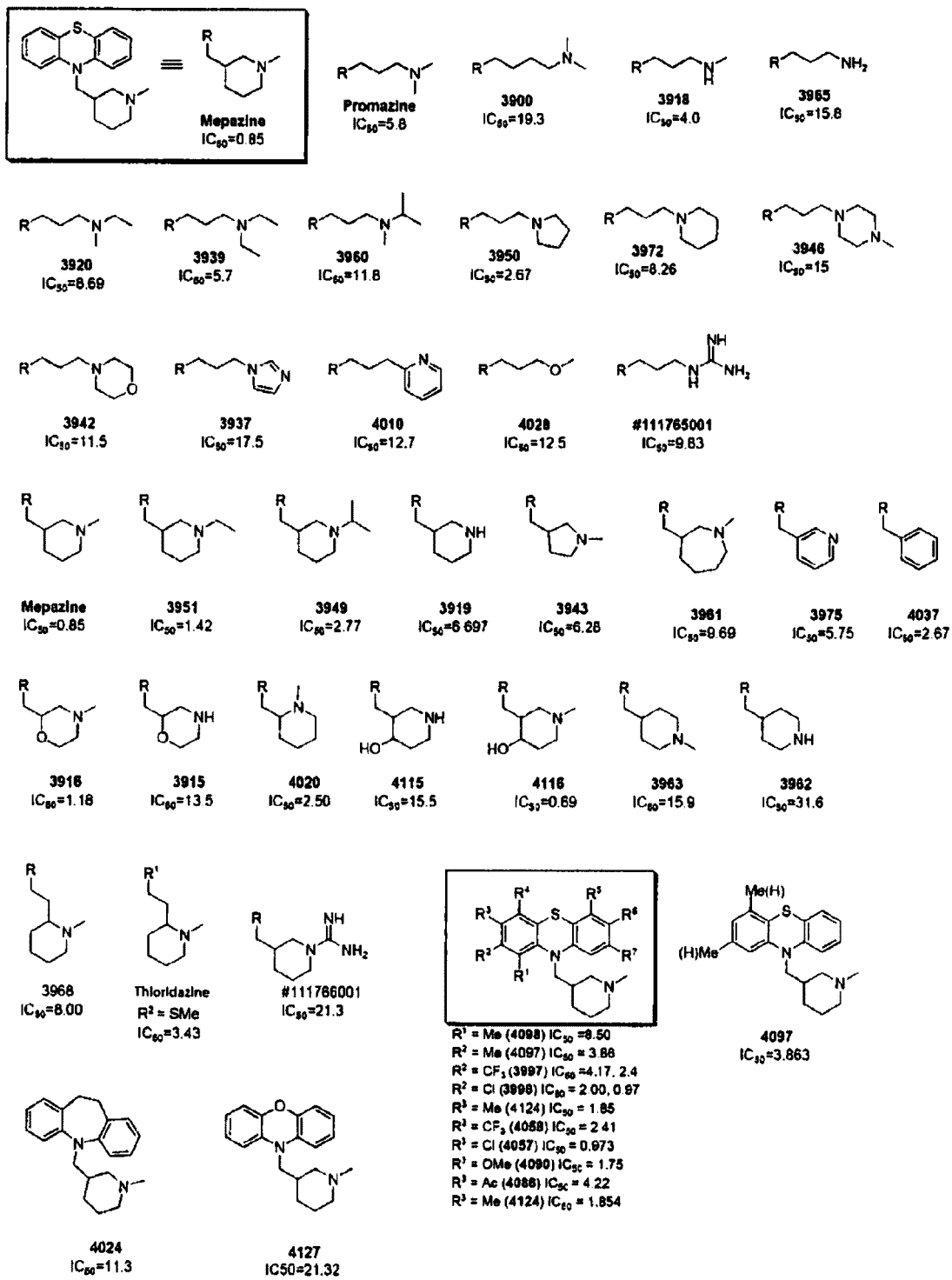

FIG. 13: Elucidation of the structure-activity-relation (SAR) of phenothiazine derivatives and MALT1. Shown are the chemical structures and the MALT1 Inhibitory potential of different phenothiazines designed by medicinal chemistry. These chemical structures fall under the ambit of the general formula (I) shown herein above. This demonstrates that compounds according to the general formula (I) are potent MALT1 Inhibitors.

THE EXAMPLES ILLUSTRATE THE INVENTION

EXAMPLE 1

Experimental Procedures

Cell Culture and Reagents

DLBCL cell lines were cultured in RPMI 1640 Medium (Invitrogen) supplemented with 20% FCS and 100 U/ml penicillin/streptomycin except the ABC line OCI-Ly10 which was cultured in IMDM (Invitrogen) with 20% human plasma, penicillin/streptomycin and 50 µM β-Mercaptoethanol. Jurkat T cells were cultured according to DLBCL cell-lines with 10% FCS. The isolation of human mononuclear cells (PBMCs) from heparin-treated (1000 U/ml) whole blood was done with Lymphoprep according to manufacturer (Axis-shield). Isolation of murine $CD4^+$ T-cells was performed with T-cell specific Dynabeads (Invitrogen). Primary cells were cultured in Jurkat media containing 50 µM β-Mercaptoethanol. Stimulation of Jurkat T cells, human PBMCs and mouse $CD4^+$ T-cells was either initiated by the addition of Phorbol 12-myristate 13-acetate (PMA; 200 ng/ml) and Ionomycin (I; 300 ng/ml) (both Calbiochem) or by hCD3/hCD28 and mIgG1/mIgG2a antibodies (BD Biosciences). Z-VRPR-FMK (Alexis Biochemicals), mepazine acetate (Chembridge), promazine hydrochloride, thioridazine hydrochloride, promethazine hydrochloride (all Sigma Aldrich) and all other PDs tested (Chembridge or Sigma) were solved in DMSO.

Recombinant and Endogenous MALT1 Cleavage Assay

GSTMALT1 proteins were produced in competent BL21 RIL *E. coli* bacteria. Protein production was induced at an $OD_{600}$ of 0.8 with 50 µM of Isopropyl-α-D-thiogalactopyranoside (IPTG) for 16 h at 18° C. Bacteria were harvested and lysed by sonication in lysis buffer (50 mM HEPES, pH 7.5, 10% Glycerol, 0.1% Triton X-100, 1 mM dithiothreitol, 150 mM NaCl, 2 mM $MgCl_2$, incl. protease inhibitors). GSTMALT1 was purified via an ÄKTA™ liquid chromatography system using Glutathione FastTrap columns (GE Healthcare). For the cleavage assay in 384-well microplates 200 ng of protein and 50 µM of the BCL-10 derived substrate Ac-LRSR-AMC was used. Following 30 min of incubation at 30° C. the fluorescence of the cleaved AMC was measured for 1 h using a Synergy 2 Microplate Reader (Biotek). Protease activity was expressed in relative fluorescence units, where DMSO treated controls were set to 100% and fluorescence of compound treated wells was calculated appropriately. Cleavage of human recombinant CASP3 (BioVision) and CASP8 (Cayman Chemical) was assayed accordingly against Ac-DEVD-AMC as substrate and 50 and 250 µg of protein, respectively. For the endogenous MALT1 protease DLBCL or Jurkat T cells ($5 \times 10^6$ cells) were left untreated, inhibitor (4 h and 3 h, respectively) or P/I and CD3/CD28 treated and lysed in lysis buffer at 4° C. For immunoprecipitation 4 µl of anti-MALT1 antibody (H-300, Santa Cruz Biotechnology) was added to 400 µl of the cleared lysate. After incubation of 16 h at 4° C. 15 µl of PBS-washed protein G-Sepharose Beads (Roche) were added and the samples were further incubated for 1 h. The beads were washed 3 times with PBS, resuspended in 40 µl of cleavage assay buffer (50 mM MES, pH 6.8, 150 mM NaCl, 10% [wt/vol] sucrose, 0.1% [wt/vol] CHAPS, 1 M ammonium citrate, 10 mM dithiothreitol) and transferred to a 384-well microwell plate. The peptide substrate Ac-LRSR-AMC was added to a final concentration of 20 µM and the activity was measured according to the recombinant GST-MALT1 assay. All inhibitors used were solved in DMSO and control cells were treated with appropriate amounts of the solvent.

High Throughput Screen (HTS) for MALT1 Small Molecule Inhibitors

The MALT1 cleavage assay was used to screen ~18000 small molecules of the ChemBioNet library at the Leibniz Institute for Molecular Pharmacology (FMP) in Berlin.[35] Screening volume was 11 µl in a 384-well non-binding assay plate (Corning) with 170 nmol GSTMALT1 against 10 µM final concentration of compounds. The assay was performed with 50 µM of Ac-LRSR-AMC substrate for 20 min at 30° C. As a negative control the recombinant MALT1 mutant C453A was used, as a medium inhibition control 1 nM of the Z-VRPR-FMK peptide. The quality of the assay was confirmed by standard Z-factor determination (~0.7). For hit validation the 300 compounds with the best inhibitory impact from the primary screen were assayed two times with 8 different concentrations of compounds ranging from 0.7 to 90.9 µM.

Quantification of RNA by Real-Time RT-PCR

Synthesis of cDNA was performed with DNA-free RNA samples (RNeasy Mini Kit, Qiagen) by reverse transcription with random hexamers and Superscript II (Invitrogen) according to the manufacturer's protocol. Real-time PCR was performed using LC 480 SybrGreen PCR mix (Roche) on a LC 480 Lightcycler system (Roche). Quantification of the cytokine RNA was achieved by normalizing to a β-Actin housekeeping gene. The relative expression ratio was calculated according to Pfaffl 2001. The following primers were used: mIL-2 forward 5'-GAGTGCCAATTCGATGAT-GAG-3' (SEQ ID NO: 1); mIL-2 reverse 5'-AGGGCTTGT-TGAGATGATGC-3' (SEQ ID NO: 2); mβ-actin forward 5'CCTCTATGCCAACACAG TGC3' (SEQ ID NO: 3); mβ-actin reverse 5'-GTACTCCTGCTTGCTGATCC-3' (SEQ ID NO: 4).[36]

Electrophoretic Mobility Shift Assay (EMSA), Western Blot and ELISA

Whole cell extracts, Western blotting and EMSA were performed as described previously.[9] Antibodies used were BCL-XL (Cell signaling), MALT1 (H300, B12), BCL10 (H197), c-FLIP (Alexis Biochemicals) and β-Actin (I-19). BCL10 cleavage was visualized after 20 h treatment of diffuse large B-cell lymphoma cells with different doses of PD. Human and murine IL-2 ELISAs (BenderMed Systems) were performed according to the manufacturers protocol after pre-treatment of Jurkat T cells and the primary human and mouse cells for 3 h with mepazine and thioridazine and subsequent T-cell receptor stimulation for 20 h. IL-6 and IL-10 ELISAs (Immunotools) were performed after 20 h of inhibitor incubation on DLBCL cell-lines.

Viability, MTT and Apoptosis Assays

Viability of DLBCL cell lines was analysed with a cell count assay of trypan blue stained cells after four days and by MTT (3-4,5-Dimethylthiazol-2-yl-2,5-diphenyltetrazoliumbromid) cytotoxicity test after two days of dose-dependent inhibitor treatment in comparison to DMSO treated control cells. The cell-dependent reduction of MTT to formazan was measured at $\lambda$=450 nm with a µQuant microplate spectrophotometer (Biotek). Apoptosis rates were determined with PE-Annexin V staining of 7AAD$^-$ cells (BD Pharmingen) by FACS analysis (LSRII, BD) after five days of compound treatment. Data was analyzed using FlowJo software (Treestar).

EXAMPLE 2

MALT1 Paracaspase Exhibits Proteolytic Activity that is Distinct from Human Caspases To screen for small molecular weight compounds that can inhibit MALT1 protease activity, recombinant GSTMALT1 was purified from *E. coli* to establish an in vitro protease cleavage assay suitable for high throughput screening (HTS). GSTMALT1 was incubated for 1 h at 30° C. in the presence of 50 µM of the tetrapeptide substrate Ac-LRSR-AMC, which is derived from the MALT1 cleavage site in the C-terminus of BCL10.[7] Proteolytic activity was determined by measuring the increase of fluorescence, which is emitted after cleavage and the accompanying release of the fluorophore AMC (FIGS. 1A and B). MALT1 catalyzed cleavage of Ac-LRSR-AMC is evident from a robust increase in fluorescence intensity over time. Mutation of the conserved cysteine (C453A) in the paracaspase domain of MALT1 (Isoform B) completely abolished MALT1 catalytic activity (FIG. 1A). Similar to arginine-lysine specific metacaspases, the MALT1 protease has a high preference for cleaving after an arginine residue. Consistent with this Z-VRPR-FMK, which was initially designed as a metacaspase antagonistic peptide,[24] also completely blocked MALT1 cleavage activity at low nanomolar concentrations, emphasizing the high similarity of the paracaspase to plant metacaspases (FIGS. 1B and C). In contrast, the potent caspase inhibitory peptide Ac-DEVD-CHO which effectively blocked CASP8 activity even at picomolar concentrations (FIG. 11) only marginally reduced MALT1 activity even when used at a concentration of 200 µM (FIG. 1D).

The distinct substrate specificity of caspases and MALT1 emphasizes the potential to identify small molecule inhibitors that interfere with MALT1 dependent pro-survival signaling[20,21] without disturbing the caspase-dependent apoptotic machinery. As MALT1 paracaspase is the only mammalian homologue to plant metacaspases,[4] the MALT1 enzymatic activity and substrate preferences was further characterized. MALT1 cleavage was assayed in the presence of protease inhibitors (FIG. 1E) and compared the effects to the inhibitory profiles obtained for plant metacaspases AtMC4 and AtMC9 as summarized in FIG. 9.[5] Just like AtMC4 and AtMC9, neither the aspartyl protease inhibitor Pepstatin A (100 µM) nor the serine protease inhibitor Aprotinin (5 µg/ml) strongly inhibited MALT1 activity. Whereas the broad spectrum serine/cysteine protease inhibitor Chymostatin (100 µM) and Antipain (1 µM) inhibited MALT1 and AtMC4/9 to a similar extent, Leupeptin (1 µM) was acting stronger on plant metacaspases. Interestingly, the cysteine protease inhibitor E-64 (100 µM) that was shown to have a mild effect on AtMC4 but not AtMC9, does not inhibit MALT1. In contrast, the serine/cysteine protease inhibitor TLCK (1 µM) that strongly inhibits AtMC9 and much weaker AtMC4, was only mildly affecting MALT1 activity. As expected, tetra-peptide caspase inhibitors did not inhibit MALT1 or AtMC4/9 activity. Taken together, substrate specificity and inhibitory profile indicate high similarity between the MALT1 paracaspase to the plant metacaspases AtMC4/9.

EXAMPLE 3

Identification of Phenothiazine Derivatives as Selective MALT1 Protease Inhibitors To identify small molecule inhibitors for the MALT1 protease, approx. 18.000 compounds of the ChemBioNet collection were screened using an assay format as depicted in FIG. 10. The primary screen was conducted by measuring the increase in AMC fluorescence in a 384 half-well format over an assay time of 20 min in the presence of 10 µM of each compound. 300 primary hits showed inhibitory potential and were chosen for secondary hit validation that was performed two times in the same format with increasing doses ranging from 0.7 to 90.9 µM of each compound. The validation yielded in 15 primary hits corresponding to ~0.08% of the primary screen.

When examining the structure of the 15 primary hits, it was noticed that three of the most efficient and selective compounds (FIG. 2A: compound A, B and C) are derivatives of the tri-cyclic phenothiazine that contains two outer benzene rings linked by a nitrogen and a sulfur atom in the inner ring. Also the heterocyclic core found in inhibitor D displays high structural similarities to phenothiazine, while the nitrogen is replaced by carbon. These initial results suggested that certain phenothiazine derivatives (PDs) may act as MALT1 inhibitors. To verify MALT1 inhibition and to evaluate the specificity, the four identified PDs were tested for inhibition of MALT1 and CASP8 activity. At 50 µM all four substances were reducing MALT1 protease activity to less than 10% in a dose-dependent manner (FIG. 2B). In contrast, CASP8 activity was only modestly affected at the highest inhibitor concentrations of 50 µM, indicating that the four PDs are selectively acting on MALT1. The phenothiazine scaffold without any modifications was also tested and it was found that it is inhibiting MALT1 activity in a dose-dependent manner (FIG. 2C). Notably, our initial results implied that only the modifications of compound A seemed to significantly improve the inhibitory potential of the phenothiazine backbone towards MALT1. Interestingly, compound A corresponds to the known drug mepazine (former brand name Pacatal) that had been used as a tranquilizer.[25] These results suggested that phenothiazines could be promising candidates as selective MALT1 inhibitors.

EXAMPLE 4

Mepazine, Thioridazine and Promazine Act as Potent and Selective MALT1 Paracaspase Inhibitors Mepazine as well as 25 other commercially available PD were obtained to test their inhibitory potential. Whereas most compounds (12-26) had no or only very weak inhibitory potential (IC50>20 µM), 8 compounds (4-11) inhibited MALT1 activity with an IC50 roughly between 5-20 µM.

Only three PD had an IC50 below 5 µM. Thus, only a small subset of PD was capable of efficiently inhibiting MALT1. The three most potent compounds represent promazine, thioridazine and mepazine, the latter initially identified in the screening (FIG. 3A). To define the inhibitory potential, the exact IC50 values for each compound on recombinant full length (FL) GSTMALT1 and an enzymatically active truncated MALT1 protein encompassing the amino acids of the paracaspase and C-terminal Ig-like (Ig3) domains from 325 to 760 was determined (FIG. 3B). Mepazine was most effective in inhibiting GSTMALT1 FL and GSTMALT1 325-760 with IC50 values of 0.83 and 0.42 µM, respectively. Also thioridazine and promazine showed a dose dependent inhibition of GSTMALT1 FL and GSTMALT1 325-760, but the IC50 values were approximately 4 (GSTMALT1 FL) or 8 (GSTMALT1 325-760) fold lower when compared to mepazine. In contrast, promethazine, a drug that is still used in the treatment of certain psychiatric disorders and highly related to the three active PD did not cause any significant MALT1 inhibition at concentrations up to 20 µM. These results indicate a high degree of specificity in MALT inhibition even within the group of PD.

To test the mode of action, the effect of mepazine in Michaelis-Menten kinetics on basis of the fluorogenic MALT1 cleavage assay was determined (FIG. 3C). GST-MALT1 FL displayed a $V_{MAX}$ of ~170 RFU/min and the Michaelis-Menten constant ($K_M$) was calculated to ~48 µM, which is in the range of what has been determined previously (Hachmann et al., 2012). Addition of mepazine at a concentration around the IC50 (1 µM) strongly decreased the $V_{MAX}$ to ~58 RFU/min while the $K_M$ of 48 µM was not altered. Mepazine and other phenothiazines do not contain reactive groups. However, to confirm that mepazine acts as a non-covalent reversible inhibitor, wash-out experiments using GSTMALT1 attached to glutathione sepharose beads were performed (FIG. 3D). Again, mepazine inhibited MALT1 cleavage activity, but several cycles of washing the GSTMALT1 beads resulted in complete loss of inhibition even at the highest concentration of the compound (50 µM). Thus, the effects of mepazine on MALT1 enzymatic activity revealed a non-competitive and reversible mode of MALT1 inhibition by phenothiazines.

Next the effects of PD on caspases, which are structurally the closest relatives of MALT1 in mammals (Uren et al., 2000) were assayed. Importantly, all three PD did not significantly inhibit CASP3 or CASP8 activity, even at concentrations up to 50 µM (FIG. 3E), reflecting the selectivity of the compounds as MALT1 inhibitors.

EXAMPLE 5

Phenothiazines Inhibit MALT1 Activity and IL-2 Induction in T Cells

Under physiological conditions the MALT1 protease has been shown to contribute to T cell responses. Mutation of the catalytic cysteine residue in the active cavity of MALT1 prevents optimal IL-2 production in response to anti-CD3/CD28 co-stimulation (Duwel et al., 2009). Therefore the effects of PD on MALT1 activity and IL-2 production in T cells were determined (FIG. 4). A MALT1 cleavage assay after immunoprecipitation (IP) of the protein from Jurkat T cells was performed (FIG. 4A). Cells were left untreated or incubated for 3 h with 10 µM of mepazine or thioridazine and subsequently left unstimulated or stimulated with anti-CD3/CD28. MALT1 protease activity was almost undetectable in the absence of stimulation and peaked at 30-60 min after CD3/CD28 treatment. Addition of either mepazine or thioridazine resulted in a strong reduction of MALT1 protease activity in stimulated Jurkat T cells at all time-points (FIG. 4A). To confirm that both phenothiazines were inhibiting MALT1 activity inside the cells, MALT1 cleavage of RelB after stimulation of Jurkat T cells was monitored (FIG. 4B). RelB cleavage product RelBΔ could be detected when Jurkat T cells were incubated with proteasome inhibitor MG132 prior to P/I stimulation to prevent degradation of the unstable RelB truncation (Hailfinger et al., 2011). As evident from decreased RelBΔ levels and a parallel increased expression of full length RelB, mepazine and thioridazine impaired RelB cleavage in a dose dependent manner (FIG. 4B). Similar to the situation with recombinant MALT1, mepazine was more efficient in inhibiting cellular MALT1 cleavage activity and significantly reduced the appearance of RelBΔ between 2-5 µM, whereas thioridazine was effective above 5 µM. To determine the effects of MALT1 inhibition by PDs on T cell activation, secreted IL-2 amounts were measured by ELISA after P/I or anti-CD3/CD28 stimulation of Jurkat T cells in the presence of absence of mepazine or thioridazine. Both compounds led to a decrease of IL-2 levels in the media of PD treated cells after T cell activation (FIG. 4C). To verify that the inhibitory potential of PD is also detectable in primary T cells, murine CD4 positive Th1 T cells were isolated and purified, and IL-2 mRNA induction by qPCR and protein levels by ELISA after anti-CD3/CD28 co-ligation in the presence or absence of 5 and 10 µM of mepazine or thioridazine were measured (FIG. 4D). Both, IL-2 mRNA induction and protein expression was reduced in a dose-dependent manner. Finally, primary human PBMCs from three donors were used to evaluate whether inhibition of MALT1 activity also promotes a decreased IL-2 production in primary human T cells (FIG. 4E). Congruent with the previous results, mepazine and thioridazine treatment led to a significant decrease of IL-2 secretion in PBMCs from all three donors.

EXAMPLE 6

Phenothiazines Inhibit MALT1 Activity and Induction of NF-κB Target Genes in ABC DLBCL Cells Coinciding with a constitutive cleavage of the MALT1 substrates A20 and BCL10, MALT1 protease activity was enhanced as a characteristic feature of all ABC-DLBCL cells was previously shown.[26] To determine the effect of phenothiazines on cellular MALT1 activity, ABC-DLBCL cells were incubated for 4 h with 5 or 10 µM of mepazine, thioridazine and promazine. An anti-MALT1 IP was performed and MALT1 protease activity was determined by adding the substrate AC-LRSR-AMC to the precipitates. All three PDs inhibited MALT1 protease activity from ABC-DLBCL cells in a dose-dependent manner (FIG. 5A). Even though inhibition of cellular MALT1 activity varied depending on the individual cell lines and the compounds, mepazine had in general the strongest effects and at 10 µM it led to at least 75% reduction of MALT1 activity in all ABC-DLBCL cells. Also thioridazine was inhibiting MALT1 activity in all ABC-DLBCL cell lines. However, whereas 10 µM thioridazine inhibited MALT1 by more than 80% in HBL1, U2932 and TMD8, only a ~50% decrease was observed in OCI-Ly3 and OCI-Ly10. Promazine was the weakest inhibitor of cellular MALT1 activity.

Next, it has been evaluated whether MALT1 inhibition by the two strongest compounds mepazine and thioridazine would also prevent the cellular cleavage of the known MALT1 substrate BCL10 in ABC-DLBCL cells (FIG. 5B). MALT1 is cleaving the very C-terminal five amino acids of BCL10 resulting in a truncated cleavage product (BCL10Δ5). ABC-DLBCL cells were treated for 20 h with increasing doses of each compound. Indeed, treatment with mepazine or thioridazine prevented the detection of BCL10Δ5 in a dose-dependent manner. MALT1 activity contributes to optimal NF-κB activation and target gene expression in ABC-DLBCL cells.[20,21] Therefore, it was determined if mepazine, which most strongly affected MALT1 activity, is also impairing constitutive NF-κB DNA binding and subsequently NF-κB target gene expression in ABC-DLBCL cells (FIG. 6). To this end DLBCL cells were treated with 10 and 20 µM of mepazine for 20 hours and analyzed NF-κB DNA binding by EMSA (FIG. 6A). Increasing concentrations of mepazine resulted in reduced NF-κB target DNA binding in ABC-DLBCL cells. Congruently, mepazine treatment led to a dose-dependent decrease of anti-apoptotic BCL-XL and FLIP-L proteins. To further monitor the effects of mepazine on other NF-κB dependent genes, ABC- or GCB-DLBCL cells were treated with 10 µM mepazine for 20 h and secretion of the cytokines IL-6 and IL-10 was determined by ELISA (FIG. 6B). Whereas GCB-DLBCL cells are expressing low amounts of IL-6 or IL-10, ABC-DLBCL cells are secreting both cytokines even though to variable extends, which reflects the degree of heterogeneity between the different cell lines. Importantly, mepazine decreased expression of soluble IL-6 and IL-10 in all ABC-, but not GCB-DLBCL cells, demonstrating its direct effect on NF-κB target gene expression.

EXAMPLE 7

Selective Toxicity and Induction of Apoptosis by Phenothiazines in ABC DLBCL Cells As the three PDs are efficiently inhibiting MALT1 protease activity in vitro and in vivo, their effect on the viability of ABC-DLBCL cells was tested (FIG. 7). As a control the three GCB-DLBCL cell lines BJAB, Su-DHL-6 and Su-DHL-4 were used, that were previously shown to be independent of MALT1 proteolytic activity for their growth and survival.[20] Cytotoxic effects were measured by MTT assays after two days of incubation (single treatment) using increasing concentrations of mepazine, thioridazine and promazine (FIG. 7A, C and FIG. 12B). All compounds promoted a decrease of cell viability measured by MTT reaction in the ABC-DLBCL cells HBL1, OCI-Ly3, U2932 and TMD8, without significantly affecting GCB-DLBCL cells. Further, cell viability was determined by cell counting after 4 days of treatment (FIG. 7B, D and FIG. 12C). Congruent with the MTT assay, the PDs also decreased the overall number of viable ABC-DLBCL cells. Again, the reduced viability was much more pronounced in ABC-DLBCL cells, while GCB-DLBCL cells were only slightly impaired even at the highest concentration of the compounds. Consistent with the results obtained in the cellular MALT1 cleavage assay (FIG. 11A), promazine had in general the mildest effects on the viability of the ABC-DLBCL cells. To further validate that the decrease in viability of ABC-DLBCL cells after administration of distinct PDs is linked to MALT1 inhibition, DLBCL cells were treated with promethazine (FIG. 12E). Despite its close structural relation to promazine, promethazine was not inhibiting MALT1 protease activity at concentrations up to 20 µM (FIG. 12D). Indeed, promethazine did not significantly inhibit viability of ABC or GCB-DLBCL cells after 4 days of treatment, providing further evidence that the cellular effects of mepazine, thioridazine and promazine are dependent on MALT1 inhibition.

Finally, it has been determined whether mepazine as the most potent MALT1 inhibitor is affecting the viability of ABC-DLBCL cells by enhancing apoptosis (FIG. 7D). To this end, DLBCL cells were treated for five days with 15 µM of mepazine and apoptotic cells were identified by FACS as AnnexinV-PE positive and 7-AAD negative cells. Mepazine provoked an enhanced apoptotic rate in all ABC-DLBCL cells, while apoptosis was not increased in the two GCB-DLBCL control cells. Thus, PDs are selectively toxic to ABC-DLBCL cells and toxicity is partially due to enhanced apoptosis in the affected lymphoma cells, revealing a potential use of mepazine and structurally related compounds for ABC-DLBCL therapy.

EXAMPLE 8

Mepazine and Thioridazine Impede Growth of ABC-DLBCL In Vivo

The long history of phenothiazine, especially thioridazine, in the treatment of psychiatric disorders as well as the detailed knowledge of their pharmacology and toxicology could facilitate an off-label use for the treatment of patients diagnosed with ABC-DLBCL. Therefore, it was determined whether mepazine and thioridazine could also exert effects on lymphoma growth in vivo in a murine DLBCL xenogeneic tumor model. For this purpose, the ABC-DLBCL cell line OCI-Ly10 and the GCB-DLBCL cell line Su-DHL-6 were injected as subcutaneous xenografts into NOD/scid IL-2Rg$^{null}$ (NSG) mice (FIG. 8A). Both tumor cell lines were engrafted simultaneously on opposite flanks of individual mice. Starting one day after injection, the mice were treated by intraperitoneal administration of solvent or either mepazine (12 mg/kg) or thioridazine (16 mg/kg). In control treated mice massive tumors grew from both DLBCL cell lines within three weeks of transplantation. Daily administration of mepazine or thioridazine strongly impaired the expansion of the ABC-DLBCL cell line OCI-Ly10. In contrast, both PD completely failed to exert any inhibitory effects on the progression of the GCB-DLBCL cell line Su-DHL-6 in the same animals.

To ascertain that mepazine and thioridazine were acting directly on the tumor cells, the induction of apoptosis in the tumor tissue was determined. Transplanted tumors were removed at the end of the treatment period and apoptotic cells were visualized by TUNEL staining on sections of the tumor tissue (FIG. 8B). Congruent with the selective in vivo toxicity, mepazine or thioridazine treatment increased the number of apoptotic cells in the xenografted ABC-DLBCL cell line OCI-Ly10, while no induction of apoptosis was observed in the in GCB-DLBCL cell line Su-DHL-6. Further, constitutive cleavage of the MALT1 substrate RelB was impaired after mepazine and thioridazine treatment in specimens of xenografted OCI-Ly10 tumors, revealing that also in mice the compounds were indeed acting by inhibiting MALT1 activity in the tumor cells (FIG. 8C). Thus, the murine tumor model provided evidence that MALT1 inhibition by phenothiazines selectively kills MALT1-dependent DLBCL in vivo and indicates a potential therapeutic benefit for use of the known compounds in ABC-DLBCL therapy.

REFERENCES

1. Thome M. Multifunctional roles for MALT1 in T-cell activation. *Nature reviews Immunology.* 2008; 8(7):495-500. Prepublished on 2008 Jun. 26 as DOI 10.1038/nri2338.
2. Scheidereit C. IkappaB kinase complexes: gateways to NF-kappaB activation and transcription. *Oncogene.* 2006; 25(51):6685-6705. Prepublished on 2006 Oct. 31 as DOI 10.1038/sj.onc.1209934.
3. Oeckinghaus A, Wegener E, Welteke V, et al. Malt1 ubiquitination triggers NF-kappaB signaling upon T-cell activation. *The EMBO journal.* 2007; 26(22):4634-4645. Prepublished on 2007 Oct. 20 as DOI 10.1038/sj.emboj.7601897.
4. Uren A G, O'Rourke K, Aravind L A, et al. Identification of paracaspases and metacaspases: two ancient families of caspase-like proteins, one of which plays a key role in MALT lymphoma. *Molecular cell.* 2000; 6(4):961-967. Prepublished on 2000 Nov. 25 as DOI.
5. Vercammen D, van de Cotte B, De Jaeger G, et al. Type II metacaspases Atmc4 and Atmc9 of *Arabidopsis thaliana* cleave substrates after arginine and lysine. *The Journal of biological chemistry.* 2004; 279(44):45329-45336. Prepublished on 2004 Aug. 25 as DOI 10.1074/jbc.M406329200.
6. Coornaert B, Baens M, Heyninck K, et al. T cell antigen receptor stimulation induces MALT1 paracaspase-mediated cleavage of the NF-kappaB inhibitor A20. *Nature immunology.* 2008; 9(3):263-271. Prepublished on 2008 Jan. 29 as DOI 10.1038/ni1561.
7. Rebeaud F, Hailfinger S, Posevitz-Fejfar A, et al. The proteolytic activity of the paracaspase MALT1 is key in T cell activation. *Nature immunology.* 2008; 9(3):272-281. Prepublished on 2008 Feb. 12 as DOI 10.1038/ni1568.
8. Staal J, Driege Y, Bekaert T, et al. T-cell receptor-induced JNK activation requires proteolytic inactivation of CYLD by MALT1. *The EMBO journal.* 2011; 30(9):1742-1752. Prepublished on 2011 Mar. 31 as DOI 10.1038/emboj.2011.85.
9. Duwel M, Welteke V, Oeckinghaus A, et al. A20 negatively regulates T cell receptor signaling to NF-kappaB by cleaving Malt1 ubiquitin chains. *Journal of immunology.* 2009; 182(12):7718-7728. Prepublished on 2009 Jun. 6 as DOI 10.4049/jimmunol.0803313.
10. Ngo V N, Davis R E, Lamy L, et al. A loss-of-function RNA interference screen for molecular targets in cancer. *Nature.* 2006; 441(7089):106-110. Prepublished on 2006 Mar. 31 as DOI 10.1038/nature04687.
11. Alizadeh A A, Eisen M B, Davis R E, et al. Distinct types of diffuse large B-cell lymphoma identified by gene expression profiling. *Nature.* 2000; 403(6769):503-511. Prepublished on 2000 Feb. 17 as DOI 10.1038/35000501.
12. Rosenwald A, Staudt L M. Gene expression profiling of diffuse large B-cell lymphoma. *Leukemia & lymphoma.* 2003; 44 Suppl 3:S41-47. Prepublished on 2004 Jun. 19 as DOI.
13. Rosenwald A, Wright G, Chan W C, et al. The use of molecular profiling to predict survival after chemotherapy for diffuse large-B-cell lymphoma. *The New England journal of medicine.* 2002; 346(25):1937-1947. Prepublished on 2002 Jun. 21 as DOI 10.1056/NEJMoa012914.
14. Savage K J, Monti S, Kutok J L, et al. The molecular signature of mediastinal large B-cell lymphoma differs from that of other diffuse large B-cell lymphomas and shares features with classical Hodgkin lymphoma. *Blood.* 2003; 102(12):3871-3879. Prepublished on 2003 Aug. 23 as DOI 10.1182/blood-2003-06-1841.
15. Wright G, Tan B, Rosenwald A, Hurt E H, Wiestner A, Staudt L M. A gene expression-based method to diagnose clinically distinct subgroups of diffuse large B cell lymphoma. *Proceedings of the National Academy of Sciences of the United States of America.* 2003; 100(17):9991-9996. Prepublished on 2003 Aug. 6 as DOI 10.1073/pnas.1732008100.
16. Staudt L M, Dave S. The biology of human lymphoid malignancies revealed by gene expression profiling. *Advances in immunology.* 2005; 87:163-208. Prepublished on 2005 Aug. 17 as DOI 10.1016/S0065-2776(05)87005-1.
17. Davis R E, Brown K D, Siebenlist U, Staudt L M. Constitutive nuclear factor kappaB activity is required for survival of activated B cell-like diffuse large B cell lymphoma cells. *The Journal of experimental medicine.* 2001; 194(12):1861-1874. Prepublished on 2001 Dec. 19 as DOI.
18. Lenz G, Davis R E, Ngo V N, et al. Oncogenic CARD11 mutations in human diffuse large B cell lymphoma. *Science.* 2008; 319(5870):1676-1679. Prepublished on 2008 Mar. 8 as DOI 10.1126/science.1153629.
19. Davis R E, Ngo V N, Lenz G, et al. Chronic active B-cell-receptor signalling in diffuse large B-cell lymphoma. *Nature.* 2010; 463(7277):88-92. Prepublished on 2010 Jan. 8 as DOI 10.1038/nature08638.
20. Ferch U, Kloo B, Gewies A, et al. Inhibition of MALT1 protease activity is selectively toxic for activated B cell-like diffuse large B cell lymphoma cells. *The Journal of experimental medicine.* 2009; 206(11):2313-2320. Prepublished on 2009 Oct. 21 as DOI 10.1084/jem.20091167.
21. Hailfinger S, Lenz G, Ngo V, et al. Essential role of MALT1 protease activity in activated B cell-like diffuse large B-cell lymphoma. *Proceedings of the National Academy of Sciences of the United States of America.* 2009; 106(47):19946-19951. Prepublished on 2009 Nov. 10 as DOI 10.1073/pnas.0907511106.
22. Isaacson P G, Du M Q. MALT lymphoma: from morphology to molecules. *Nature reviews Cancer.* 2004; 4(8):644-653. Prepublished on 2004 Aug. 3 as DOI 10.1038/nrc1409.
23. Rosebeck S, Madden L, Jin X, et al. Cleavage of NIK by the API2-MALT1 fusion oncoprotein leads to noncanonical NF-kappaB activation. *Science.* 2011; 331(6016):468-472. Prepublished on 2011 Jan. 29 as DOI 10.1126/science.1198946.
24. Vercammen D, Belenghi B, van de Cotte B, et al. Serpin1 of *Arabidopsis thaliana* is a suicide inhibitor for metacaspase 9. *Journal of molecular biology.* 2006; 364(4):625-636. Prepublished on 2006 Oct. 10 as DOI 10.1016/j.jmb.2006.09.010.
25. Whittier J R, Klein D F, Levine G, Weiss D. Mepazine (pacatal): clinical trial with placebo control and psychological study. *Psychopharmacologia.* 1960; 1:280-287. Prepublished on 1960 Jun. 23 as DOI.
26. Kloo B, Nagel D, Pfeifer M, et al. Critical role of PI3K signaling for NF-kappaB-dependent survival in a subset of activated B-cell-like diffuse large B-cell lymphoma cells. *Proceedings of the National Academy of Sciences of the United States of America.* 2011; 108(1):272-277. Prepublished on 2010 Dec. 22 as DOI 10.1073/pnas.1008969108.
27. Su H, Bidere N, Zheng L, et al. Requirement for caspase-8 in NF-kappaB activation by antigen receptor.

28. Choi J H, Yang Y R, Lee S K, et al. Potential inhibition of PDK1/Akt signaling by phenothiazines suppresses cancer cell proliferation and survival. *Annals of the New York Academy of Sciences*. 2008; 1138:393-403. Prepublished on 2008 Oct. 8 as DOI 10.1196/annals.1414.041.
29. Rho S B, Kim B R, Kang S. A gene signature-based approach identifies thioridazine as an inhibitor of phosphatidylinositol-3'-kinase (PI3K)/AKT pathway in ovarian cancer cells. *Gynecologic oncology*. 2011; 120(1):121-127. Prepublished on 2010 Nov. 3 as DOI 10.1016/j.ygyno.2010.10.003.
30. Seeman P, Lee T, Chau-Wong M, Wong K. Antipsychotic drug doses and neuroleptic/dopamine receptors. *Nature*. 1976; 261(5562):717-719. Prepublished on 1976 Jun. 24 as DOI.
31. Sarwer-Foner G J, Koranyi E K. The clinical investigation of pacatal in open psychiatric settings. *Canadian Medical Association journal*. 1957; 77(5):450-459. Prepublished on 1957 Sep. 1 as DOI.
32. Zhelev Z, Ohba H, Bakalova R, et al. Phenothiazines suppress proliferation and induce apoptosis in cultured leukemic cells without any influence on the viability of normal lymphocytes. Phenothiazines and leukemia. *Cancer chemotherapy and pharmacology*. 2004; 53(3):267-275. Prepublished on 2003 Dec. 10 as DOI 10.1007/s00280-003-0738-1.
33. van Soolingen D, Hernandez-Pando R, Orozco H, et al. The antipsychotic thioridazine shows promising therapeutic activity in a mouse model of multidrug-resistant tuberculosis. *PloS one*. 2010; 5(9). Prepublished on 2010 Sep. 17 as DOI 10.1371/journal.pone.0012640.
34. Weisman J L, Liou A P, Shelat A A, Cohen F E, Guy R K, DeRisi J L. Searching for new antimalarial therapeutics amongst known drugs. *Chemical biology & drug design*. 2006; 67(6):409-416. Prepublished on 2006 Aug. 3 as DOI 10.1111/j.1747-0285.2006.00391.x.
35. Lisurek M, Rupp B, Wichard J, et al. Design of chemical libraries with potentially bioactive molecules applying a maximum common substructure concept. *Molecular diversity*. 2010; 14(2):401-408. Prepublished on 2009 Aug. 18 as DOI 10.1007/s11030-009-9187-z.
36. Yin M, Zhang L, Sun X M, Mao L F, Pan J. Lack of apoE causes alteration of cytokines expression in young mice liver. *Molecular biology reports*. 2010; 37(4):2049-2054. Prepublished on 2009 Aug. 1 as DOI 10.1007/s11033-009-9660-x.

The invention claimed is:

1. A method for treating a disease that depends on the activity of the MALT1 protease in a human subject in need thereof, wherein said disease is selected from a cancer that is the activated B-cell subtype of diffuse-large B cell lymphoma or MALT lymphoma, comprising administering an effective amount of a compound having the formula (I)

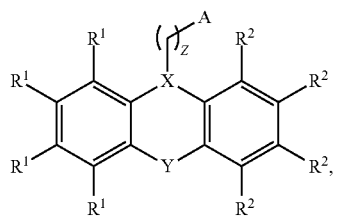

I wherein
X is N;
Y is S;
( )$_z$ is a $C_1$-$C_5$ linear or branched alkyl chain;
A is $NR^3R^4$, or $OR^5$, or HET;
$R^1$ and $R^2$ in each occurrence are independently selected from —H, —$CH_3$, —OH, —$OCH_3$, —$SCH_3$, —F, —Cl, —$CF_3$, —$NH_2$, and —COOH;
$R^3$, $R^4$, and $R^5$ are H, or $C_1$-$C_5$ linear or branched alkyl groups, and
HET is a heterocyclic ring of 5, 6, or 7 members, wherein the ring atoms can be C, O, N, or S, the ring can be saturated or aromatic, and the ring can be substituted with H or $C_1$-$C_5$ linear or branched alkyl groups; or
a pharmaceutically acceptable salt, enantiomer, diastereomer, racemic mixture, or solvate of said compound.

2. The method according to claim 1, wherein
( )$_z$ is a linear $C_1$-$C_5$ alkyl chain
$R^1$ is —H; and
$R^2$ is —H or —$SCH_3$.

3. The method according to claim 2, wherein A is HET and HET is a 5-membered to 7-membered carbocyclic ring which is interrupted with $NR^3$.

4. The method according to claim 2, wherein A is $NR^3R^4$ and $R^3$ is H or $CH_3$ and $R^4$ is —$CH_3$.

5. The method according to claim 2, wherein A is $NR^3R^4$, wherein $R^3$ is $CH_3$, $R^4$ is —$CH_3$, —$C_2H_5$, or a $C_3$-$C_5$ linear alkyl chain the chain of which may be interrupted by O, N or S and which forms a saturated ring with a carbon atom of ( )$_z$.

6. The method according to claim 5, wherein the saturated ring is a 5-membered to 7-membered carbocyclic ring which is interrupted with N.

7. The method according to claim 3, wherein A is HET and HET is N-Methylpiperidin-2-yl or N-Methylpiperidin-3-yl.

8. The method according to claim 1, wherein
(a) Z=3, A is $NR^3R^4$, and $R^3$ and $R^4$ are —$CH_3$;
(b) Z=1 and A is N-methylpiperidin-3-yl; or
(c) Z=2 and A is N-methylpiperidin-2-yl.

9. The method according to claim 1, wherein the compound is

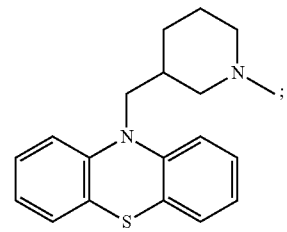

;

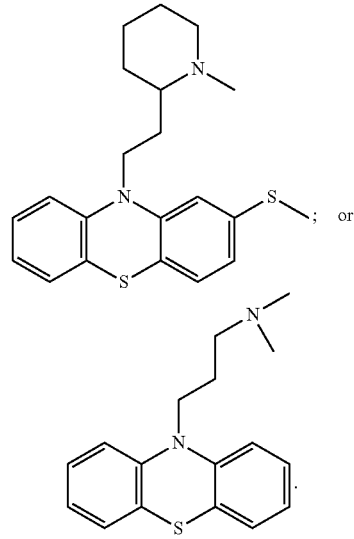

; or

10. The method according to claim 1, wherein the compound is

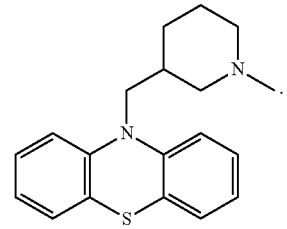 [SMILES: CN1CCCC(CN2c3ccccc3Sc3ccccc32)C1]

.

11. The method according to claim 1, wherein the compound is

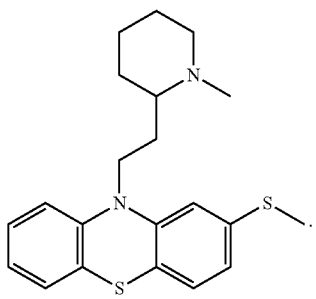 [SMILES: CSc1ccc2c(c1)N(CCC1CCCCN1C)c1ccccc1S2]

12. The method according to claim 1, wherein the compound is

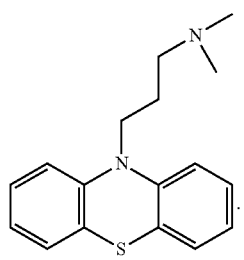 [SMILES: CN(C)CCCN1c2ccccc2Sc2ccccc21]

13. A method for inhibiting the activity of the MALT1 protease in a human subject in need thereof, wherein said activity is connected to a disease selected from a cancer that is the activated B-cell subtype of diffuse-large B cell lymphoma or MALT lymphoma, comprising administering an effective amount of a compound having the formula (I)

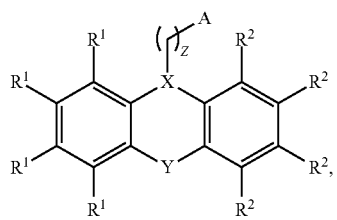

wherein
X is N;
Y is S;
( )$_z$ is a $C_1$-$C_5$ linear or branched alkyl chain;
A is $NR^3R^4$, or $OR^5$, or HET;
$R^1$ and $R^2$ in each occurrence are independently selected from —H, —$CH_3$, —OH, —$OCH_3$, —$SCH_3$, —F, —Cl, —$CF_3$, —$NH_2$, and —COOH;
$R^3$, $R^4$, and $R^5$ are H, or $C_1$-$C_5$ linear or branched alkyl groups, and
HET is a heterocyclic ring of 5, 6, or 7 members, wherein the ring atoms can be C, O, N, or S, the ring can be saturated or aromatic, and the ring can be substituted with H or $C_1$-$C_5$ linear or branched alkyl groups; or
a pharmaceutically acceptable salt, enantiomer, diastereomer, racemic mixture, or solvate of said compound.

14. A method for treating a disease that depends on the activity of the MALT1 protease in a human subject in need thereof, wherein said disease is selected from a MALT1-dependent immune disease that is multiple sclerosis, psoriasis, or rheumatoid arthritis, comprising administering an effective amount of the compound

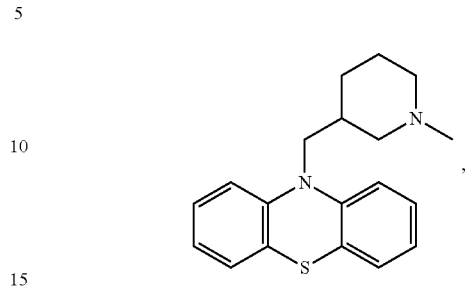

or a pharmaceutically acceptable salt, enantiomer, diastereomer, racemic mixture, or solvate of said compound.

15. A method for treating a disease that depends on the activity of the MALT1 protease in a human subject in need thereof, wherein said disease is selected from a MALT1-dependent immune disease that is multiple sclerosis, psoriasis, or rheumatoid arthritis, comprising administering an effective amount of the compound

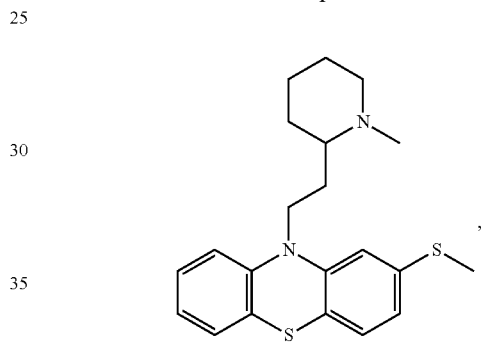

or a pharmaceutically acceptable salt, enantiomer, diastereomer, racemic mixture, or solvate of said compound.

16. A method for treating a disease that depends on the activity of the MALT1 protease in a human subject in need thereof, wherein said disease is selected from a MALT1-dependent immune disease that is multiple sclerosis, psoriasis, or rheumatoid arthritis, comprising administering an effective amount of the compound

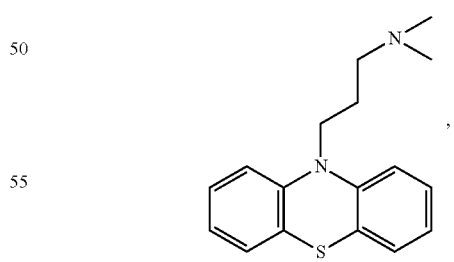

or a pharmaceutically acceptable salt, or solvate of said compound.

17. A method for treating a disease that depends on the activity of the MALT1 protease in a human subject in need thereof, wherein said disease is selected from a MALT1-dependent immune disease that is multiple sclerosis, psoriasis, or rheumatoid arthritis, comprising administering an effective amount of a compound having the formula (I)

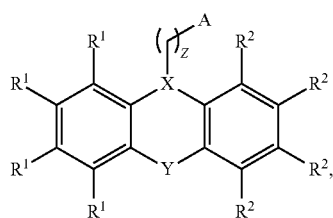

wherein
X is N;
Y is S;
(i) ( )$_z$ is a $C_3$-$C_4$ linear alkyl chain and A is $NR^3R^4$ or $OR^5$; or;
(ii) ( )$_z$ is a $C_1$-$C_2$ linear alkyl chain and A is HET
$R^1$ and $R^2$ in each occurrence are independently selected from —H, —CH$_3$, —OH, —OCH$_3$, —SCH$_3$, —F, —Cl and —CF$_3$;
$R^3$, $R^4$, and $R^5$ are H, or $C_1$-$C_3$ linear or branched alkyl groups, and
HET is a heterocyclic ring of 5, 6, or 7 members, wherein the ring atoms can be C, O or N, the ring includes at least 1 N atom, can be saturated or aromatic, and the ring can be substituted with H or $C_1$-$C_2$ linear or branched alkyl groups; or
a pharmaceutically acceptable salt, enantiomer, diastereomer, racemic mixture, or solvate of said compound.

18. A method for inhibiting the activity of the MALT1 protease in a human subject in need thereof, wherein said activity is connected to a disease selected from a MALT1-dependent immune disease that is multiple sclerosis, psoriasis, or rheumatoid arthritis, comprising administering an effective amount of a compound having the formula (I)

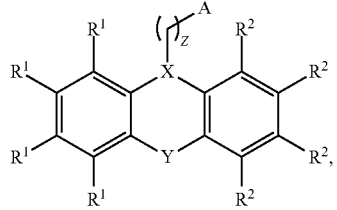

wherein
X is N;
Y is S;
(i) ( )$_z$ is a $C_3$-$C_4$ linear alkyl chain and A is $NR^3R^4$ or $OR^5$; or;
(ii) ( )$_z$ is a $C_1$-$C_2$ linear alkyl chain and A is HET
$R^1$ and $R^2$ in each occurrence are independently selected from —H, —CH$_3$, —OH, —OCH$_3$, —SCH$_3$, —F, —Cl and —CF$_3$;
$R^3$, $R^4$, and $R^5$ are H, or $C_1$-$C_3$ linear or branched alkyl groups, and
HET is a heterocyclic ring of 5, 6, or 7 members, wherein the ring atoms can be C, O or N, the ring includes at least 1 N atom, can be saturated or aromatic, and the ring can be substituted with H or $C_1$-$C_2$ linear or branched alkyl groups; or
a pharmaceutically acceptable salt, enantiomer, diastereomer, racemic mixture, or solvate of said compound.

19. A method for treating a disease that depends on the activity of the MALT1 protease in a human subject in need thereof, wherein said disease is selected from a cancer that is the activated B-cell subtype of diffuse-large B cell lymphoma or MALT lymphoma, comprising administering an effective amount of the compound

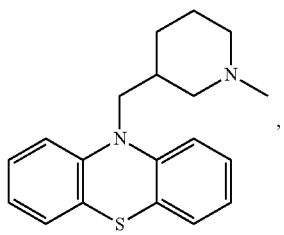 [SMILES: CN1CCCC(CN2c3ccccc3Sc3ccccc32)C1]

or a pharmaceutically acceptable salt, enantiomer, diastereomer, racemic mixture, or solvate of said compound.

20. A method for treating a disease that depends on the activity of the MALT1 protease in a human subject in need thereof, wherein said disease is selected from a cancer that is the activated B-cell subtype of diffuse-large B cell lymphoma or MALT lymphoma, comprising administering an effective amount of the compound

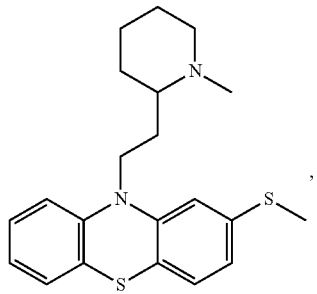 [SMILES: CSc1ccc2c(c1)N(CCC1CCCCN1C)c1ccccc1S2]

or a pharmaceutically acceptable salt, enantiomer, diastereomer, racemic mixture, or solvate of said compound.

21. A method for treating a disease that depends on the activity of the MALT1 protease in a human subject in need thereof, wherein said disease is selected from a cancer that is the activated B-cell subtype of diffuse-large B cell lymphoma or MALT lymphoma, comprising administering an effective amount of the compound

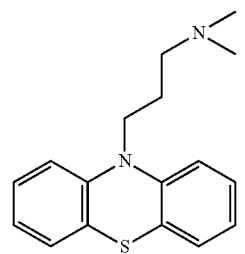

or a pharmaceutically acceptable salt, or solvate of said compound.

* * * * *

```
                       SEQUENCE LISTING

<160> NUMBER OF SEQ ID NOS: 4

<210> SEQ ID NO 1
<211> LENGTH: 21
<212> TYPE: DNA
<213> ORGANISM: artificial sequence
<220> FEATURE:
<223> OTHER INFORMATION: /note="Description of artificial sequence:
      mIL-2 forward primer"

<400> SEQUENCE: 1
gagtgccaat tcgatgatga g                                            21

<210> SEQ ID NO 2
<211> LENGTH: 20
<212> TYPE: DNA
<213> ORGANISM: artificial sequence
<220> FEATURE:
<223> OTHER INFORMATION: /note="Description of artificial sequence:
      mIL-2 reverse primer"

<400> SEQUENCE: 2
agggcttgtt gagatgatgc                                              20

<210> SEQ ID NO 3
<211> LENGTH: 20
<212> TYPE: DNA
<213> ORGANISM: artificial sequence
<220> FEATURE:
<223> OTHER INFORMATION: /note="Description of artificial sequence:
      mbeta-actin forward primer"

<400> SEQUENCE: 3
cctctatgcc aacacagtgc                                              20

<210> SEQ ID NO 4
<211> LENGTH: 20
<212> TYPE: DNA
```

```
<213> ORGANISM: artificial sequence
<220> FEATURE:
<223> OTHER INFORMATION: /note="Description of artificial sequence:
      mbeta-actin reverse primer"

<400> SEQUENCE: 4
gtactcctgc ttgctgatcc                                                20
```